United States Patent
Simón et al.

(10) Patent No.: US 12,285,439 B2
(45) Date of Patent: Apr. 29, 2025

(54) METHODS FOR DIAGNOSING AND/OR TREATING ACUTE OR CHRONIC LIVER, KIDNEY OR LUNG DISEASE

(71) Applicant: ASOCIACIÓN CENTRO DE INVESTIGACIÓN COOPERATIVA EN BIOCIENCIAS-CIC bioGUNE, Vizcaya (ES)

(72) Inventors: Jorge Simón, Bizkaia (ES); María Luz Martínez Chantar, Bizkaia (ES); Alfonso Martínez De La Cruz, Bizkaia (ES)

(73) Assignee: ASOCIACIÓN CENTRO DE INVESTIGACIÓN COOPERATIVA EN BIOCIENCIAS-CIC BIOGUNE, Vizcaya (ES)

( * ) Notice: Subject to any disclaimer, the term of this patent is extended or adjusted under 35 U.S.C. 154(b) by 874 days.

(21) Appl. No.: 17/297,045

(22) PCT Filed: Nov. 26, 2019

(86) PCT No.: PCT/EP2019/082606
§ 371 (c)(1),
(2) Date: May 26, 2021

(87) PCT Pub. No.: WO2020/109316
PCT Pub. Date: Jun. 4, 2020

(65) Prior Publication Data
US 2022/0026444 A1 Jan. 27, 2022

(30) Foreign Application Priority Data
Nov. 26, 2018 (EP) .................................. 18382853

(51) Int. Cl.
| | | |
|---|---|---|
| A61K 31/713 | (2006.01) |
| A61P 1/16 | (2006.01) |
| A61P 11/00 | (2006.01) |
| A61P 13/12 | (2006.01) |
| C12N 15/113 | (2010.01) |

(52) U.S. Cl.
CPC ............. *A61K 31/713* (2013.01); *A61P 1/16* (2018.01); *A61P 11/00* (2018.01); *A61P 13/12* (2018.01); *C12N 15/113* (2013.01); *C12N 2310/122* (2013.01); *C12N 2310/14* (2013.01); *C12N 2310/531* (2013.01)

(58) Field of Classification Search
None
See application file for complete search history.

(56) References Cited

U.S. PATENT DOCUMENTS

| | | |
|---|---|---|
| 6,537,749 B2 | 3/2003 | Kuimelis et al. |
| 8,697,359 B1 | 4/2014 | Zhang |
| 2003/0039958 A1 | 2/2003 | Holt et al. |
| 2018/0170946 A1 | 6/2018 | Lazo et al. |

FOREIGN PATENT DOCUMENTS

| | | |
|---|---|---|
| WO | 9951773 A1 | 10/1999 |
| WO | 0140803 A1 | 6/2001 |
| WO | WO 2017174657 A1 | 10/2017 |
| WO | WO 2018185253 A1 | 10/2018 |
| WO | WO 2020109316 A1 | 6/2020 |

OTHER PUBLICATIONS

Jarald et al., "Nucleic acid drugs: A novel approach", African Journal of Biotechnology vol. 3, Published Dec. 2004, pp. 662-666. (Year: 2004).*
Hirata Y et al., Mg-dependent Interactions of ATP with the Cystathionine-beta-Synthase (CBS) Domains of a Magnesium Transporter, The Journal of Biological Chemistry, 2014, vol. 289, No. 21, pp. 14731-14739.
Rao DD et al., siRNA vs. shRNA: Similarities and differences, 2009, Advanced Drug Delivery Reviews, 61, 746-759.
Yuchen Nan and Yan-Jin Zhang, 2018, Antisense Phosphorodiamidate Morpholino Oligomers as Novel Antiviral Compounds, Frontiers in Microbiology, vol. 9, Art 750.
Jonathan K. Watts and David R. Corey, Gene silencing by siRNAs and antisense oligonucleotides in the laboratory and the clinic, 2012, J Pathol., 226(2): 365-379.
Lam JKW et al., siRNA Versus miRNA as Therapeutics for Gene Silencing, 2015, Molecular Therapy—Nucleic Acids 4, e252.
Tao Y et al., Application of nanoparticle-based siRNA and CRISPR/Cas9 delivery systems in gene-targeted therapy, 2018, Nanomedicine, DOI: 10.2217/nnm-2018-0522.
Foster DJ et al., Comprehensive evaluation of canonical versus Dicer-substrate siRNA in vitro and in vivo, 2012, RNA, 18(3):557-68.
Kruspe S and Paloma H. Giangrande, Aptamer-siRNA Chimeras: Discovery, Progress, and Future Prospects, 2017, Biomedicines, Aug. 9;5(3):45.
Karnati HK et al., Therapeutic potential of siRNA and DNAzymes in cancer, 2014, Tumor Biology, DOI 10.1007/s13277-014-2477-9.
Sioud M 2006, Ribozymes and siRNAs: From Structure to Preclinical Applications, HEP 2006, 173: 223-242.

(Continued)

*Primary Examiner* — Brian Whiteman
*Assistant Examiner* — Stephanie L Sullivan
(74) *Attorney, Agent, or Firm* — Casimir Jones, S.C.; Tristan A. Fuierer

(57) ABSTRACT

The present invention relates to a CNNM4 inhibitor for use in the treatment of an acute or a chronic liver, kidney and/or lung disease in a subject, and to pharmaceutical compositions comprising a therapeutically effective amount of a CNNM4 inhibitor and a pharmaceutically acceptable excipient or carrier. Furthermore, the invention relates to a method for diagnosing a liver disease, a kidney disease or a lung disease in a subject, and to in vitro methods for identifying a compound potentially useful for reducing an induced CNNM4-mediated disease or condition in a cell.

3 Claims, 9 Drawing Sheets

Specification includes a Sequence Listing.

(56) References Cited

OTHER PUBLICATIONS

Ramareddy, et al., Triplex-forming oligonucleotides as modulators of gene expression, The International Journal of Biochemistry & Cell Biology 25: 22-31.
Funato et al., "Membrane protein CNNM4-dependent MG2+ efflux suppresses tumor progression," 2014. J Clin Invest. 124(12):5398-5410.
Chothia, C. et al., "Canonical Structures for Hypervariable Regions of Immunoglobulins," (1987) J. Mol. Biol. 196:901-917.
James, G. L. et al., "Benzodiazepine Peptidomimetics: Potent Inhibitors of Ras Farnesylation in Animal Cells," (1993) Science 260: 1937-1942.
Binz et al., "Engineering novel binding proteins from nonimmunoglobulin domains," 2005, Nat. Biotech. 23:1257-68.
Yamazaki D, et al., "Basolateral Mg2+ Extrusion via CNNM4 mediates Transcellular Mg2+ Transport across Epithelia: A Mouse Model," (2013), PLoS Genet 9(12): e1003983.
Que-Gewirth NS, "Gene therapy progress and prospects: RNA aptamers," Gene Ther. Feb. 2007;14(4):283-91.
Oney S, "Antidote-Controlled Platelet Inhibition Targeting von Willebrand Factor with Aptamers," Oligonucleotides, 2007, 17(3):265-74.
Park, H., et al., "Discovery of novel PRL-3 ibhibitors based on the structure-based virtual screening," 2008. Bioorg Med Chem Lett. 18(7):2250-5.
Davis, M. E. et al., "Evidence of RNAi in humans from systemically administered siRNA via targeted nanoparticles," Nature Apr. 15, 2010; 464(7291), 1067-1070.
De Wildt et al., "Antibody arrays for high-throughput screening of antibody-antigen interactions," (2000) Nat. Biotechnol. 18:989-994.
Lueking et al., "Protein Microarrays for Gene Expression and Antibody Screening," (1999) Anal. Biochem. 270:103-111.
Ge, "UPA, a universal protein array system for quantitative detection of protein-protein, protein-DNA, protein-RNA and protein-ligand interactions," (2000) Nucleic Acids Res. vol. 28, No. E3, 2000, pp. I-VII.
MacBeath et al., "Printing Proteins as Microarrays for High-Throughput Function Determination," (2000) Science 289:1760-1763.
Fernández-Álvarez et al., "TRAIL-producing NK cells contribute to liver injury and related fibrogenesis in the context of GNMT deficiency," 2015. Lab Invest. 95(2):223-36.
Wagner et al., "Hepatocellular Carcinoma in GNMT −/− mice," 2009. Toxicol Appl Pharmacol. 237(2):246; author reply 247.
Folch et al., "A Simple Method for the Isolation and Purification of Total Lipides from Animal Tissues," 1957. J Biol Chem. 226(1):497-509.
Ruiz et al., "Quantification in the subnanomolar range of phospholipids and neutral lipids by monodimensional thin-layer chromatography and image analysis," Journal of Lipid Research, 1997, vol. 38, 1482-1489.
Gruskos et al., "Visualizing Compartmentalized Cellular Mg2+ on Demand with Small-Molecule Fluorescent Sensors," 2016. J. Am. Chem. Soc. 138 (44), pp. 14639-14649.
Grynkiewicz et al., "A New Generation of Ca2+ Indicators with Greatly Improved Fluorescence Properties," 1985. J Biol Chem. 260(6):3440-50.
Daouti et al., "A Selective Phosphatase of Regenerating Liver Phosphatase Inhibitor Suppresses Tumor Cell Anchorage-Independent Growth by a Novel Mechanism Involving p130Cas Cleavage," Cancer Research, vol. 68, No. 4, Aug. 15, 2008, pp. 1162-1169.
International Search Report for PCT/EP2019/082606, Feb. 21, 2020.
Wei et al., Targeting phosphatases of regenerating liver (PRLs) in cancer, Pharmacology & Therapeutics, Oct. 2018, vol. 190, pp. 128-138.
Funato et al., Membrane protein CNNM4-dependent Mg2+ efflux suppresses tumor progression, The Journal of Clinical Investigation, vol. 124, No. 12, Oct. 27, 2014, pp. 5398-5410.
Funato et al., Molecular function and biological importance of CNNM family Mg2+ transporters, Journal of Biochemistry, vol. 165, No. 3, Nov. 11, 2018, pp. 219-225.
Simón et al., Magnesium accumulation upon cyclin M4 silencing activates microsomal triglyceride transfer protein improving NASH, Feb. 9, 2021, vol. 75, No. 1, pp. 34-45.
Weingärtner et al., Less Is More: Novel Hepatocyte-Targeted siRNA Conjugates for Treatment of Liver-Related Disorders, Molecular Therapy: Nucleic Acids., vol. 21, Sep. 1, 2020, pp. 242-250.
Yamazaki et al., Basolateral Mg2+ Extrusion via CNNM4 Mediates Transcellular Mg2+ Transport across Epithelia: A Mouse Model, PLOS Genetics, vol. 9, No. 12, Dec. 5, 2013 (Dec. 5, 2013), p. e1003983.
Hardy S., et al., "Physiological and Oncogenic Roles of the PRL Phosphatases", The Federation of European Biochemical Societies Journal, vol. 285, 2018, pp. 3886-3908.

\* cited by examiner

A

B

SEQUENCE LISTING

```
<160> NUMBER OF SEQ ID NOS: 56

<210> SEQ ID NO 1
<211> LENGTH: 21
<212> TYPE: DNA
<213> ORGANISM: Artificial sequence
<220> FEATURE:
<223> OTHER INFORMATION: CNNM1 sense

<400> SEQUENCE: 1
gauccugaau gcuguaauat t                                                   21

<210> SEQ ID NO 2
<211> LENGTH: 21
<212> TYPE: DNA
<213> ORGANISM: Artificial sequence
<220> FEATURE:
<223> OTHER INFORMATION: CNNM1 antisense

<400> SEQUENCE: 2
uauuacagca uucaggaucc g                                                   21

<210> SEQ ID NO 3
<211> LENGTH: 21
<212> TYPE: DNA
<213> ORGANISM: Artificial sequence
<220> FEATURE:
<223> OTHER INFORMATION: CNNM1 sense

<400> SEQUENCE: 3
acgugaucca ggagcuuaat t                                                   21

<210> SEQ ID NO 4
<211> LENGTH: 21
<212> TYPE: DNA
<213> ORGANISM: Artificial sequence
<220> FEATURE:
<223> OTHER INFORMATION: CNNM1 antisense

<400> SEQUENCE: 4
uuaagcuccu ggaucacgut g                                                   21

<210> SEQ ID NO 5
<211> LENGTH: 21
<212> TYPE: DNA
<213> ORGANISM: Artificial sequence
<220> FEATURE:
<223> OTHER INFORMATION: CNNM2 sense
```

```
<400> SEQUENCE: 5
ctcaatttgc atgaaattta a                                              21

<210> SEQ ID NO 6
<211> LENGTH: 21
<212> TYPE: DNA
<213> ORGANISM: Artificial sequence
<220> FEATURE:
<223> OTHER INFORMATION: CNNM2 antisense

<400> SEQUENCE: 6
uuaaauuuca ugcaaauuga g                                              21

<210> SEQ ID NO 7
<211> LENGTH: 21
<212> TYPE: DNA
<213> ORGANISM: Artificial sequence
<220> FEATURE:
<223> OTHER INFORMATION: CNNM2 sense

<400> SEQUENCE: 7
cggagaaaga gaagaauuat t                                              21

<210> SEQ ID NO 8
<211> LENGTH: 21
<212> TYPE: DNA
<213> ORGANISM: Artificial sequence
<220> FEATURE:
<223> OTHER INFORMATION: CNNM2 antisense

<400> SEQUENCE: 8
uaauucuucu cuuucuccgt g                                              21

<210> SEQ ID NO 9
<211> LENGTH: 21
<212> TYPE: DNA
<213> ORGANISM: Artificial sequence
<220> FEATURE:
<223> OTHER INFORMATION: CNNM3 sense

<400> SEQUENCE: 9
gaugaugaau auaaaguaat t                                              21

<210> SEQ ID NO 10
<211> LENGTH: 21
<212> TYPE: DNA
<213> ORGANISM: Artificial sequence
<220> FEATURE:
<223> OTHER INFORMATION: CNNM3 antisense

<400> SEQUENCE: 10
uuacuuuaua uucaucauca g                                              21

<210> SEQ ID NO 11
<211> LENGTH: 21
<212> TYPE: DNA
<213> ORGANISM: Artificial sequence
<220> FEATURE:
<223> OTHER INFORMATION: CNNM3 sense

<400> SEQUENCE: 11
gggcagaguc gaggucgaat t                                              21

<210> SEQ ID NO 12
<211> LENGTH: 21
```

```
<212> TYPE: DNA
<213> ORGANISM: Artificial sequence
<220> FEATURE:
<223> OTHER INFORMATION: CNNM3 antisense

<400> SEQUENCE: 12
uucgaccucg acucugcccu g                                            21

<210> SEQ ID NO 13
<211> LENGTH: 21
<212> TYPE: DNA
<213> ORGANISM: Artificial sequence
<220> FEATURE:
<223> OTHER INFORMATION: CNNM4 sense

<400> SEQUENCE: 13
cacuauuguu cucaccaaat t                                            21

<210> SEQ ID NO 14
<211> LENGTH: 21
<212> TYPE: DNA
<213> ORGANISM: Artificial sequence
<220> FEATURE:
<223> OTHER INFORMATION: CNNM4 antisense

<400> SEQUENCE: 14
uuuggugaga acaauagugt t                                            21

<210> SEQ ID NO 15
<211> LENGTH: 20
<212> TYPE: DNA
<213> ORGANISM: Artificial sequence
<220> FEATURE:
<223> OTHER INFORMATION: Arp forward

<400> SEQUENCE: 15
cgacctggaa gtccaactac                                              20

<210> SEQ ID NO 16
<211> LENGTH: 18
<212> TYPE: DNA
<213> ORGANISM: Artificial sequence
<220> FEATURE:
<223> OTHER INFORMATION: Arp reverse

<400> SEQUENCE: 16
atctgctgca tctgcttg                                                18

<210> SEQ ID NO 17
<211> LENGTH: 20
<212> TYPE: DNA
<213> ORGANISM: Artificial sequence
<220> FEATURE:
<223> OTHER INFORMATION: Cnnm1 forward

<400> SEQUENCE: 17
caacgagggt gaaggagacc                                              20

<210> SEQ ID NO 18
<211> LENGTH: 20
<212> TYPE: DNA
<213> ORGANISM: Artificial sequence
<220> FEATURE:
<223> OTHER INFORMATION: Cnnm1 reverse

<400> SEQUENCE: 18
```

-continued cgtcgaggat ctccgacttg                                              20

<210> SEQ ID NO 19
<211> LENGTH: 20
<212> TYPE: DNA
<213> ORGANISM: Artificial sequence
<220> FEATURE:
<223> OTHER INFORMATION: Cnnm2 forward

<400> SEQUENCE: 19
gcgaggctat cctggacttc                                              20

<210> SEQ ID NO 20
<211> LENGTH: 20
<212> TYPE: DNA
<213> ORGANISM: Artificial sequence
<220> FEATURE:
<223> OTHER INFORMATION: Cnnm2 reverse

<400> SEQUENCE: 20
tgttggaacg ttctccctcg                                              20

<210> SEQ ID NO 21
<211> LENGTH: 20
<212> TYPE: DNA
<213> ORGANISM: Artificial sequence
<220> FEATURE:
<223> OTHER INFORMATION: Cnnm3 forward

<400> SEQUENCE: 21
ctatcgttga gcccgaggac                                              20

<210> SEQ ID NO 22
<211> LENGTH: 20
<212> TYPE: DNA
<213> ORGANISM: Artificial sequence
<220> FEATURE:
<223> OTHER INFORMATION: Cnnm3 reverse

<400> SEQUENCE: 22
ggacagcgtc cagtttggta                                              20

<210> SEQ ID NO 23
<211> LENGTH: 19
<212> TYPE: DNA
<213> ORGANISM: Artificial sequence
<220> FEATURE:
<223> OTHER INFORMATION: Cnnm4 forward

<400> SEQUENCE: 23
aggtgaacaa tgagggcga                                               19

<210> SEQ ID NO 24
<211> LENGTH: 21
<212> TYPE: DNA
<213> ORGANISM: Artificial sequence
<220> FEATURE:
<223> OTHER INFORMATION: Cnnm4 reverse

<400> SEQUENCE: 24
ccgggtccga ttatcagtgt a                                            21

<210> SEQ ID NO 25
<211> LENGTH: 25
<212> TYPE: RNA
<213> ORGANISM: Artificial Sequence

```
<220> FEATURE:
<223> OTHER INFORMATION: human CNNM4 siRNA target sequence

<400> SEQUENCE: 25
gcgagagcau gaagcuguau gcacu                                             25

<210> SEQ ID NO 26
<211> LENGTH: 21
<212> TYPE: RNA
<213> ORGANISM: Artificial Sequence
<220> FEATURE:
<223> OTHER INFORMATION: Mouse CNNM4 siRNA sequence n1 FW

<400> SEQUENCE: 26
gaacugagaa ggagagaaau u                                                 21

<210> SEQ ID NO 27
<211> LENGTH: 21
<212> TYPE: RNA
<213> ORGANISM: Artificial Sequence
<220> FEATURE:
<223> OTHER INFORMATION: Mouse CNNM4 siRNA sequence n1 RV

<400> SEQUENCE: 27
uuucucuccu ucucaguucu u                                                 21

<210> SEQ ID NO 28
<211> LENGTH: 21
<212> TYPE: RNA
<213> ORGANISM: Artificial Sequence
<220> FEATURE:
<223> OTHER INFORMATION: Mouse CNNM4 siRNA sequence n2 FW

<400> SEQUENCE: 28
gggagaagcu gauggagauu u                                                 21

<210> SEQ ID NO 29
<211> LENGTH: 21
<212> TYPE: RNA
<213> ORGANISM: Artificial Sequence
<220> FEATURE:
<223> OTHER INFORMATION: Mouse CNNM4 siRNA sequence n2 RV

<400> SEQUENCE: 29
aucuccauca gcuucuccccu u                                                21

<210> SEQ ID NO 30
<211> LENGTH: 21
<212> TYPE: RNA
<213> ORGANISM: Artificial Sequence
<220> FEATURE:
<223> OTHER INFORMATION: Mouse CNNM4 siRNA sequence n3 FW

<400> SEQUENCE: 30
caaugaacuc aaagugaaau u                                                 21

<210> SEQ ID NO 31
<211> LENGTH: 21
<212> TYPE: RNA
<213> ORGANISM: Artificial Sequence
<220> FEATURE:
<223> OTHER INFORMATION: Mouse CNNM4 siRNA sequence n3 RV

<400> SEQUENCE: 31
uuucacuuug aguucauugu u                                                 21
```

```
<210> SEQ ID NO 32
<211> LENGTH: 21
<212> TYPE: RNA
<213> ORGANISM: Artificial Sequence
<220> FEATURE:
<223> OTHER INFORMATION: Mouse CNNM4 siRNA sequence n4 FW

<400> SEQUENCE: 32
cgggagaagc ugauggagau u                                              21

<210> SEQ ID NO 33
<211> LENGTH: 21
<212> TYPE: RNA
<213> ORGANISM: Artificial Sequence
<220> FEATURE:
<223> OTHER INFORMATION: Mouse CNNM4 siRNA sequence n4 RV

<400> SEQUENCE: 33
ucuccaucag cuucucccgu u                                              21

<210> SEQ ID NO 34
<211> LENGTH: 21
<212> TYPE: RNA
<213> ORGANISM: Artificial Sequence
<220> FEATURE:
<223> OTHER INFORMATION: Mouse CNNM4 siRNA sequence n5 FW

<400> SEQUENCE: 34
uggugaagga ggaguuaaau u                                              21

<210> SEQ ID NO 35
<211> LENGTH: 21
<212> TYPE: RNA
<213> ORGANISM: Artificial Sequence
<220> FEATURE:
<223> OTHER INFORMATION: Mouse CNNM4 siRNA sequence n5 RV

<400> SEQUENCE: 35
uuuaacuccu ccuucaccau u                                              21

<210> SEQ ID NO 36
<211> LENGTH: 21
<212> TYPE: RNA
<213> ORGANISM: Artificial Sequence
<220> FEATURE:
<223> OTHER INFORMATION: Mouse CNNM4 siRNA sequence n6 FW

<400> SEQUENCE: 36
gugaaggagg aguuaaauau u                                              21

<210> SEQ ID NO 37
<211> LENGTH: 21
<212> TYPE: RNA
<213> ORGANISM: Artificial Sequence
<220> FEATURE:
<223> OTHER INFORMATION: Mouse CNNM4 siRNA sequence n6 RV

<400> SEQUENCE: 37
uauuuaacuc cuccuucacu u                                              21

<210> SEQ ID NO 38
<211> LENGTH: 21
<212> TYPE: RNA
<213> ORGANISM: Artificial Sequence
<220> FEATURE:
<223> OTHER INFORMATION: Human CNNM4 siRNA sequence n1 FW
```

```
<400> SEQUENCE: 38
gauuguagcu guuaagaaau u                                        21

<210> SEQ ID NO 39
<211> LENGTH: 21
<212> TYPE: RNA
<213> ORGANISM: Artificial Sequence
<220> FEATURE:
<223> OTHER INFORMATION: Human CNNM4 siRNA sequence n1 RV

<400> SEQUENCE: 39
uuucuuaaca gcuacaaucu u                                        21

<210> SEQ ID NO 40
<211> LENGTH: 21
<212> TYPE: RNA
<213> ORGANISM: Artificial Sequence
<220> FEATURE:
<223> OTHER INFORMATION: Human CNNM4 siRNA sequence n2 FW

<400> SEQUENCE: 40
aggcagagcu caagggagau u                                        21

<210> SEQ ID NO 41
<211> LENGTH: 21
<212> TYPE: RNA
<213> ORGANISM: Artificial Sequence
<220> FEATURE:
<223> OTHER INFORMATION: Human CNNM4 siRNA sequence n2 RV

<400> SEQUENCE: 41
ucucccuuga gcucugccuu u                                        21

<210> SEQ ID NO 42
<211> LENGTH: 21
<212> TYPE: RNA
<213> ORGANISM: Artificial Sequence
<220> FEATURE:
<223> OTHER INFORMATION: Human CNNM4 siRNA sequence n3 FW

<400> SEQUENCE: 42
gauuguagcu guuaagaaau u                                        21

<210> SEQ ID NO 43
<211> LENGTH: 21
<212> TYPE: RNA
<213> ORGANISM: Artificial Sequence
<220> FEATURE:
<223> OTHER INFORMATION: Human CNNM4 siRNA sequence n3 RV

<400> SEQUENCE: 43
uuucuuaaca gcuacaaucu u                                        21

<210> SEQ ID NO 44
<211> LENGTH: 21
<212> TYPE: RNA
<213> ORGANISM: Artificial Sequence
<220> FEATURE:
<223> OTHER INFORMATION: Human CNNM4 siRNA sequence n4 FW

<400> SEQUENCE: 44
cgauggagau uuagaguauu u                                        21

<210> SEQ ID NO 45
```

-continued

```
<211> LENGTH: 21
<212> TYPE: RNA
<213> ORGANISM: Artificial Sequence
<220> FEATURE:
<223> OTHER INFORMATION: Human CNNM4 siRNA sequence n4 RV

<400> SEQUENCE: 45
auacucuaaa ucuccaucgu u                                              21

<210> SEQ ID NO 46
<211> LENGTH: 21
<212> TYPE: RNA
<213> ORGANISM: Artificial Sequence
<220> FEATURE:
<223> OTHER INFORMATION: Human CNNM4 siRNA sequence n5 FW

<400> SEQUENCE: 46
gcugaugagu gcaaagaaau u                                              21

<210> SEQ ID NO 47
<211> LENGTH: 21
<212> TYPE: RNA
<213> ORGANISM: Artificial Sequence
<220> FEATURE:
<223> OTHER INFORMATION: Human CNNM4 siRNA sequence n5 RV

<400> SEQUENCE: 47
uuucuuugca cucaucagcu u                                              21

<210> SEQ ID NO 48
<211> LENGTH: 21
<212> TYPE: RNA
<213> ORGANISM: Artificial Sequence
<220> FEATURE:
<223> OTHER INFORMATION: Human CNNM4 siRNA sequence n6 FW

<400> SEQUENCE: 48
ccucaaagcu caaggcacau u                                              21

<210> SEQ ID NO 49
<211> LENGTH: 21
<212> TYPE: RNA
<213> ORGANISM: Artificial Sequence
<220> FEATURE:
<223> OTHER INFORMATION: Human CNNM4 siRNA sequence n6 RV

<400> SEQUENCE: 49
ugugccuuga gcuuugaggu u                                              21

<210> SEQ ID NO 50
<211> LENGTH: 21
<212> TYPE: DNA
<213> ORGANISM: Artificial Sequence
<220> FEATURE:
<223> OTHER INFORMATION: CNNM4 (homo sapiens) sense

<400> SEQUENCE: 50
ccaugucgga gauaauggat t                                              21

<210> SEQ ID NO 51
<211> LENGTH: 21
<212> TYPE: DNA
<213> ORGANISM: Artificial Sequence
<220> FEATURE:
<223> OTHER INFORMATION: CNNM4 (homo sapiens) antisense

<400> SEQUENCE: 51
```

```
uccauuaucu ccgacauggt g                                              21

<210> SEQ ID NO 52
<211> LENGTH: 29
<212> TYPE: DNA
<213> ORGANISM: Artificial Sequence
<220> FEATURE:
<223> OTHER INFORMATION: shRNA sequence

<400> SEQUENCE: 52
tctctgcctt caaggatgcg gacaatgag                                      29

<210> SEQ ID NO 53
<211> LENGTH: 20
<212> TYPE: DNA
<213> ORGANISM: Artificial Sequence
<220> FEATURE:
<223> OTHER INFORMATION: Arp (homo sapiens) forward

<400> SEQUENCE: 53
cgacctggaa gtccaactac                                                20

<210> SEQ ID NO 54
<211> LENGTH: 18
<212> TYPE: DNA
<213> ORGANISM: Artificial Sequence
<220> FEATURE:
<223> OTHER INFORMATION: Arp (homo sapiens) reverse

<400> SEQUENCE: 54
atctgctgca tctgcttg                                                  18

<210> SEQ ID NO 55
<211> LENGTH: 20
<212> TYPE: DNA
<213> ORGANISM: Artificial Sequence
<220> FEATURE:
<223> OTHER INFORMATION: CNNM4 (homo sapiens) forward

<400> SEQUENCE: 55
gagctgcaac aactcgtgtg                                                20

<210> SEQ ID NO 56
<211> LENGTH: 20
<212> TYPE: DNA
<213> ORGANISM: Artificial Sequence
<220> FEATURE:
<223> OTHER INFORMATION: CNNM4 (homo sapiens) reverse

<400> SEQUENCE: 56
tccacctcgg tgaaggagat                                                20
```

METHODS FOR DIAGNOSING AND/OR TREATING ACUTE OR CHRONIC LIVER, KIDNEY OR LUNG DISEASE

CROSS-REFERENCE TO RELATED APPLICATIONS

This application is filed under the provisions of 35 U.S.C. § 371 and claims the priority of International Patent Application No. PCT/EP2020/051048 filed on 16 Jan. 2020 entitled "THERAPEUTIC NANOCONJUGATES AND USES THEREOF" in the name of Antonio VILLAVERDE CORRALES, et al., which claims priority to European Patent Application No. 19382031.3, filed on 17 Jan. 2019, both of which are hereby incorporated by reference herein in their entirety.

INCORPORATION BY REFERENCE

In compliance with 37 C.F.R. § 1.52(e)(5), the sequence information contained in electronic file name "383_sequence_listing_ST25.txt," size 11499 bytes, created on May 26, 2021 using Patent-In 3.5, is hereby incorporated by reference in its entirety.

TECHNICAL FIELD OF THE INVENTION

The present invention relates to the field of diagnosing and treating acute or chronic diseases. More particularly, it relates to the use of CNNM4 as a marker of said diseases and to inhibitors of CNNM4 for treating liver, kidney and lung disease.

BACKGROUND OF THE INVENTION

Chronic liver disease comprehends a group of hepatic pathologies from different etiology. Non-alcoholic fatty liver disease (NAFLD), with an incidence of 20-30% in global population, includes a spectrum of disorders in liver that go from steatosis, a simple lipid accumulation, to the development of steatohepatitis (NASH), characterized by a steatosis with inflammation and occasionally, fibrosis. Although NAFLD is a rather benign and reversible pathology, about 20% of NASH patients develop cirrhosis. Importantly, cirrhosis is an irreversible pathology characterized by an extracellular matrix deposition which causes liver dysfunction. Finally, approximately a quarter of fibrotic patients develop hepatocellular carcinoma (HCC), the most frequent form of liver cancer and the fifth cause of morbidity and mortality in the world. At the diagnosis moment very few patients are eligible for therapeutic intervention and survival rates are really poor, with only 6-20 months survival after diagnosis.

On another hand, liver can suffer from acute damage. This organ plays a central role in drug metabolism and clearance and, in case of a drug overdose, drug-induced liver injury (DILI) can be developed. This pathology is the main cause of acute liver failure and transplantation in the USA and most of Europe. About 30000 patients per year develop acetaminophen (APAP)-induced liver injury and the 29% of them undergo liver transplantation. Until nowadays, the standard therapy is just the one based of treating them with N-acetylcysteine but it has a lower chance of rescuing the liver so other therapies are needed.

Taking into account the wide group of liver pathologies and the incidence of them among the population, not only in terms of health but also economically, the development of new effective treatments is required. It also must be mentioned that it is a rather asymptomatic disease during its previous stages, so apart from treatments diagnosis tools are required for detecting the disease as soon as possible in order to stop the progression.

Renal fibrosis results of an excessive accumulation of extracellular matrix (ECM) occurring in almost every kind of chronic liver disease. Similarly as in liver the pathogenesis is a progressive process that leads to an end-stage renal failure, a devastating disorder that requires dialysis or kidney transplantation. The process of ECM development and accumulation can be caused by two alterations. On one hand, several cellular pathways have been identified as the major avenues for the generation of ECM-producing cells in diseased conditions and, on the other hand, defective matrix degradation where the exact action and mechanism of ECM-degrading enzymes have been increasingly complicated. Although many therapeutic interventions appear effective in animal models, the translation of these promising results into humans remains ineffective.

Pulmonary fibrosis is a disease resulting in a damage and scarring of lung tissue. The thickened and stiffness lead to difficulties, where breathing becomes shorter as fibrosis worsens. In most cases, the cause of the pathology remains unknown so it is normally known as idiopathic pulmonary fibrosis (IPF). Although over recent years antifibrotic therapies have been developed, several efforts are being made at identifying key biomarkers that may direct to find more specific treatment.

SUMMARY OF THE INVENTION

The inventors have surprisingly found that CNNM4 is overexpressed in a group of different pathologies, both in human samples and in animal models. This pathologies comprise chronic liver pathologies such as NASH, cirrhosis and HCC, or acute pathologies such as DILI. CNNM4 overexpression in a renal fibrosis mouse model has also been observed. The inventors have also found that CNNM4 inhibition reduces the levels of biomarker indicators in animal models for said diseases.

Thus, in a first aspect, the invention refers to a CNNM4 inhibitor for use in medicine.

In a further aspect, the invention refers to a CNNM4 inhibitor for use in the treatment of an acute or a chronic disease in a subject, wherein the disease is selected from the group consisting of a liver disease, a kidney disease and a lung disease.

In another aspect, the invention refers to an in vitro method for diagnosing liver disease, kidney disease or lung disease in a subject which comprises:
(a) determining the expression level of CNNM4 in a sample from said subject, and
(b) comparing said level with a reference value,
wherein an increased expression level of CNNM4 in said sample with respect to the reference value is indicative that the patient suffers from a liver disease, a kidney disease or a lung disease.

In yet another aspect, the invention refers to the use of a reagent specific for determining the expression level of CNNM4, for in vitro diagnosing a liver disease, a kidney disease or a lung disease in a subject.

In an additional aspect, the invention refers to an in vitro method of reducing an induced disease or condition in a cell, the method comprising contacting the cell with a specific CNNM4 inhibitor in an amount effective to decrease a CNNM4 activity, level or function in the cell.

In a final aspect, the invention refers to an in vitro method for identifying a compound potentially useful for reducing an induced CNNM4-mediated disease or condition in a cell, the method comprising contacting the cell with a candidate compound in an amount effective to decrease a CNNM4 activity, level or function in the cell, or in an amount effective to reduce the relative lipid accumulation or to reduce the relative mitochondrial ROS with respect to a reference value, wherein a candidate compound that inhibits CNNM4 activity, reduces the relative lipid accumulation with respect to a reference value or reduces the relative mitochondrial ROS with respect to a reference value in an induced CNNM4-mediated disease or condition in a cell is identified as a compound potentially useful for treating and/or preventing a CNNM4-mediated liver, kidney and/or lung disease.

DETAILED DESCRIPTION OF THE INVENTION

Figure 1:
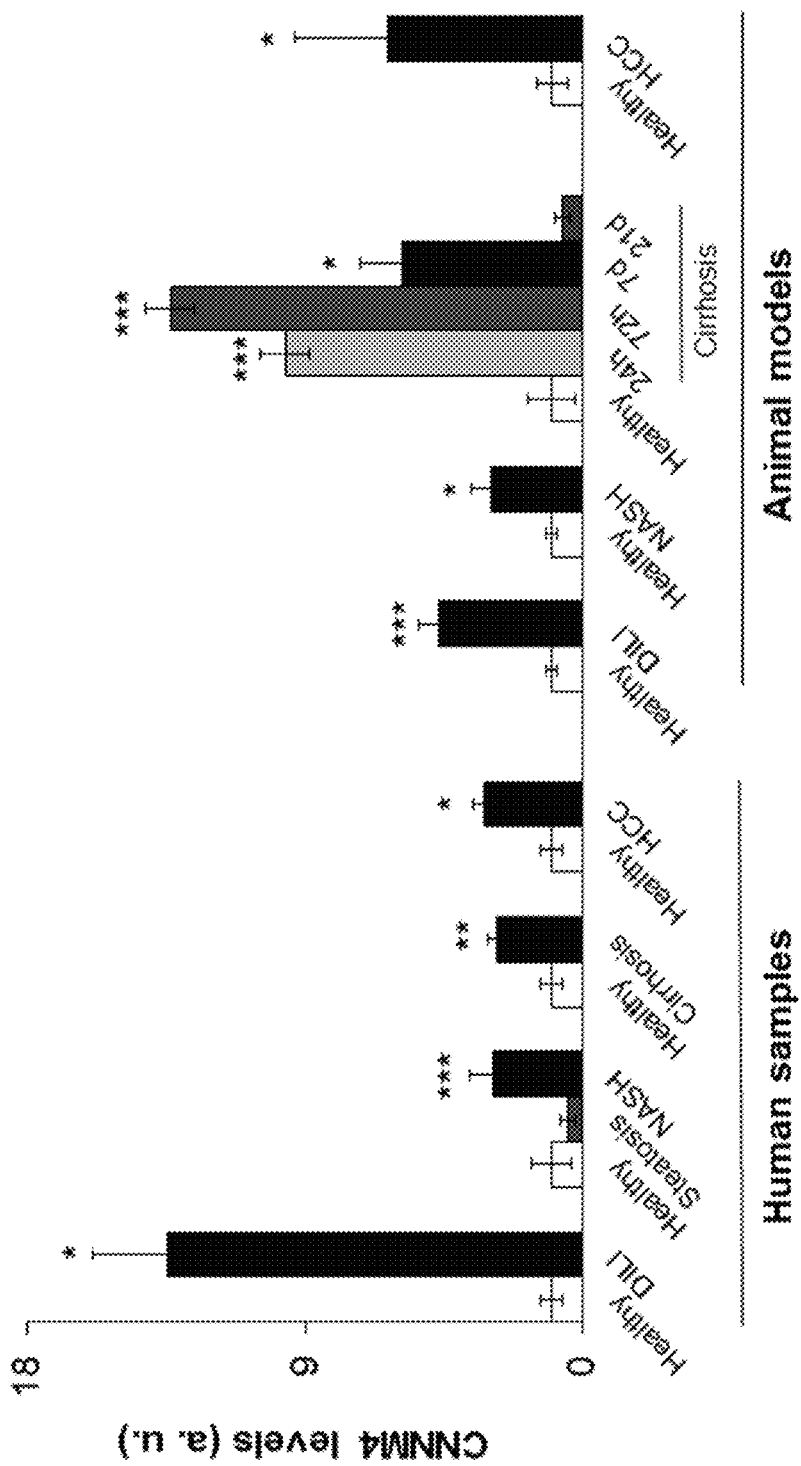
FIG. 1. CNNM4 expression in liver determined by IHC in human samples and mouse models from DILI and different pathologies of chronic liver disease. $*p<0.05$ vs Healthy; $p<0.01$ vs Healthy; $*p<0.001$ vs Healthy.

As mentioned previously, the inventors have surprisingly found that CNNM4 is overexpressed in a group of different pathologies, both in human samples and in animal models. These pathologies comprise chronic liver pathologies such as NASH, cirrhosis and HCC, or acute pathologies such as DILI. CNNM4 overexpression in a renal fibrosis mouse model has also been observed. The inventors have also found that CNNM4 inhibition reduces the levels of biomarker indicators in animal models for said diseases.

Medical uses of CNNM4 inhibitors Thus, in a first aspect, the invention relates to a CNNM4 inhibitor for use in medicine (i.e. for use as a medicament).

In a second aspect the invention relates to a CNNM4 inhibitor for use in the treatment of an acute or a chronic disease in a subject, wherein the disease is selected from the group consisting of a liver disease, a kidney disease and a lung disease.

As it is used herein the term "CNNM4" means "Cyclin and CBS domain divalent metal cation transport mediator" (also known as Ancient Conserved Domain Protein, ACDP, Cyclin M or CNNM). CNNMs are membrane proteins encoded by four genes, CNNM1, CNNM2, CNNM3 and CNNM4 that are evolutionary expressed throughout development and in all adult tissues, except for CNNM1 which is mainly expressed in the brain. CNNMs play a key role in the transport of magnesium ions (Mg2+) through the cell membranes in different organs (Funato et al., 2014. *J Clin Invest.* 124(12):5398-5410). CNNM4 corresponds to the human gene identified by ID number ENSG00000158158 in the Ensembl database (according to release 93 of July 2018). According to the Ensembl database, CNNM4 encodes at least 4 transcript or splice variants. Thus, the disclosure relates to variant CNNM4-201 (ENST00000377075.2) and to the other three variants CNNM4-204 (ENST00000496186.5), CNNM4-203 (ENST00000493384.1) and CNNM4-202 (ENST00000482716.5). CNNM4 gene encodes the protein "Metal transporter CNNM4" identified by the Uniprot Database as Q6P4Q7 (according to version 130 of Oct. 10, 2018).

As it is used herein, the term "inhibitor" is understood as any substance or compound which is capable of specifically silencing, reducing, preventing and/or blocking the expression of the gene, either by preventing the transcription of the gene CNNM4, therefore avoiding the formation of any of the transcriptional products of the gene, or by promoting the degradation of any of the transcriptional products of the gene CNNM4, or by specifically reducing, preventing and/or blocking the expression of the encoded protein, as well as any compound that inhibits the activity of the CNNM4 protein. In one embodiment, the CNNM4 inhibitor is any substance or compound which is capable of specifically silencing, reducing, preventing and/or blocking the expression of the gene, either by preventing the transcription of the gene CNNM4, therefore avoiding the formation of any of the transcriptional products of the gene, or by promoting the degradation of any of the transcriptional products of the gene CNNM4, or by specifically reducing, preventing and/or blocking the expression of the encoded protein.

The term "transcriptional product" or "transcript", as used herein, refers to an RNA derived from the transcription of a gene.

The expression of a protein or nucleic acid is considered to be reduced when its levels decrease with respect to the reference value by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100% (i.e., absent). The reference value refers to the level of an mRNA or protein in control subject, which may be a subject who does not suffer a specific disease and who is generally considered to be healthy. Alternatively, the reference value may refer to the level of an mRNA or protein in the subject before administration of an inhibitor. In the context of the present invention, the reference value refers to the protein or mRNA level of CNNM4 in a control subject or in the subject before administration of an inhibitor. In an embodiment, the control subject is a subject who does not suffer from a liver, kidney or lung disease.

The activity of the CNNM4 protein is considered to be inhibited when said activity decreases with respect to a reference value by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100% (i.e., absent). In an embodiment, the reference value refers to the activity of the CNNM4 protein in a sample from a control subject, which may be a subject who does not suffer from a specific disease and who is generally considered to be healthy. Alternatively, the reference value refers to the activity of the CNNM4 protein in a sample from the subject before administration of a CNNM4 inhibitor. In the context of the present invention, the reference value refers to the CNNM4 protein activity in a control subject or in the subject but before administration of a CNNM4 inhibitor. In an embodiment, the control subject is a subject who does not suffer from a liver, kidney or lung disease.

"Reference value", as used herein relates to a laboratory value used as a reference for the values/data obtained from samples. The reference value (or reference level) can be an absolute value, a relative value, a value which has an upper and/or lower limit, a series of values, an average value, a median, a mean value, or a value expressed by reference to a control or reference value. A reference value can be based on the value obtained from an individual sample, such as, for example, a value obtained from a sample of study but obtained at a previous point in time. The reference value can be based on a high number of samples, such as the values obtained in a population of samples or based on a pool of samples including or excluding the sample to be tested.

Methods suitable for determining the expression level of CNNM4 are known in the art, and include any method suitable for determining the expression of CNNM4 gene and/or its protein levels. In a particular embodiment, the reference value is the level of the mRNA transcribed from the CNNM4 gene in the absence of the inhibitor of the invention.

Methods suitable for determining the expression level of CNNM4 gene include, without limitation, standard assays for determining mRNA expression levels such as qPCR, RT-PCR, RNA protection analysis, Northern blot, RNA dot blot, in situ hybridization, microarray technology, tag based methods such as serial analysis of gene expression (SAGE) including variants such as LongSAGE and SuperSAGE, microarrays, fluorescence in situ hybridization (FISH), including variants such as Flow-FISH, qFiSH and double fusion FISH (D-FISH), and the like.

Methods suitable for determining the expression level of CNNM4 protein include, without limitation, quantification by means of conventional methods, for example, using antibodies capable of binding specifically to CNNM4 protein and the subsequent quantification of the resulting antibody-antigen complexes. There is a wide range of well-known assays which can be used in the present invention, using non-labelled antibodies (primary antibody) and labelled antibodies (secondary antibody); these techniques include, among others, Western blot, ELISA (enzyme-linked immunosorbent assay), RIA (radioimmunoassay), competitive EIA (competitive enzyme immunoassay), DAS-ELISA (double antibody sandwich ELISA), immunocytochemical and immunohistochemical techniques, techniques based on the use of biochips or protein microarrays including specific antibodies, or assays based on colloidal precipitation in formats such as dipsticks. Other ways of detecting and quantifying the levels of the protein of interest include affinity chromatography techniques, ligand binding assays, etc.

In a preferred embodiment, the inhibitor of expression of CNNM4 is selected from the group consisting of a protein, a nucleic acid, a small molecule or a combination thereof. Alternatively, the inhibitor of expression of CNNM4 is selected from the group consisting of a protein, a nucleic acid, or a combination thereof. Preferably, the inhibitor of expression of CNNM4 is selected from the group consisting of a neutralizing antibody or functional fragment thereof, an antagonist, a soluble binding protein, a soluble receptor variant, a non-functional derivative, an antisense polynucleotide, a RNA interference oligonucleotide, a phosphorodiamidate morpholino oligomer (PMO), miRNA, siRNA, methylated siRNA, treated siRNAs, shRNA, antisense RNA, a dicer-substrate 27-mer duplex, an aptamer, a DNAzyme, a ribozyme, a triplex forming oligonucleotide (TFO), a small molecule and combinations thereof.

In an embodiment the inhibitor of CNNM4 is a neutralizing antibody or a functional fragment thereof. As it is used herein, the term "antibody" refers to a protein including at least one immunoglobulin variable region, for example, an amino acid sequence providing an immunoglobulin variable domain or a sequence of the immunoglobulin variable domain. A "functional fragment" is any fragment of an antibody able to maintain its capacity to inhibit CNNM4. An antibody can include, for example, a variable heavy chain (H) region (herein abbreviated as VH) and a variable light chain (L) region (herein abbreviated as VL). Typically, an antibody includes two variable heavy chain regions and two variable light chain regions. The term "antibody" encompasses antigen-binding antibody fragments (for example, single-chain antibodies, nanobodies (VHH), Fab fragments, F(ab')2 fragments, Fd fragments, Fv fragments and dAb fragments) as well as whole antibodies, for example, intact and/or full length immunoglobulins of the IgA, IgG types (for example, IgG1, IgG2, IgG3, IgG4), IgE, IgD, IgM (as well as subtypes thereof). The variable heavy and light chain regions can additionally be subdivided into hypervariability regions, referred to as "complementarity determining regions" ("CDR"), mixed together with more conserved regions, referred to as "framework regions" (FR). The extension of FRs and CDRs has been precisely defined (see Kabat, E. A., et al. (1991) Sequences of Proteins of Immunological Interest, Fifth Edition, The United States Department of Health and Human Services, NIH Publication No. 91-3242; and Chothia, C. et al. (1987) J. Mol. Biol. 196: 901-917). Kabat definitions are used in the present document. Each variable heavy and light chain region is typically made up of three CDRs and four FRs, organized from the amino end to the carboxyl end in the following order: FR1, CDR1, FR2, CDR2, FR3, CDR3, FR4. The antibody VH or VL chain can furthermore include all or part of a heavy chain or light chain constant region to thereby form a heavy chain (HC) or light chain (LC immunoglobulin, respectively. Immunoglobulin light and heavy chains can be bound by disulfide bridges.

The heavy chain constant region typically includes three constant domains, CH1, CH2 and CH3. The light chain constant region typically includes a CL domain. The variable heavy and light chain region contains a binding domain interacting with an antigen. The constant regions of the antibodies typically mediate the binding of the antibody to host tissues or factors, including various cells of the immune system (for example, effector cells) and the first component (C1q) of the conventional complement system. The term antibody encompasses both antibodies formed by heavy chains and light chains and single-chain antibodies.

As it is used herein, the term "heavy chain" or "HC" encompasses both a full length heavy chain and fragments thereof. A full length heavy chain includes a variable region domain, VH, and three constant region domains, CH1, CH2 and CH3. The VH domain is at the amino terminal end of the polypeptide, and the CH3 domain is at the carboxyl terminal end.

As it is used herein, the term "light chain" encompasses a full length light chain and fragments thereof. A full length light chain includes a variable region domain, VL, and a constant region domain, CL. Like the heavy chain, the variable light chain region domain is at the amino terminal end of the polypeptide.

As it is used herein, the term "single-chain antibody" refers to a molecule modified by means of genetic engineering containing the variable light chain region and the variable heavy chain region bound by means of a suitable peptide linker, formed as a genetically fused single-chain molecule.

As it is used herein, the term "nanobody" refers to a single-domain antibody (sdAb), which is an antibody fragment consisting of a single monomeric variable antibody domain. Like a whole antibody, it is able to bind selectively to a specific antigen.

As it is used herein, the term "antibody mimetic" refers to any compound that, like antibodies, can specifically bind antigens, but that are not necessarily structurally related to antibodies. A "mimetic" of a compound includes compounds in which chemical structures of the compound necessary for functional activity have been replaced with other chemical structures which mimic the conformation of the compound. Examples of mimetics include peptidic compounds in which the peptide backbone is substituted with one or more benzodiazepine molecules (see e.g., James, G. L. et al. (1993) Science 260: 1937-1942) or oligomers that mimics peptide secondary structure through use of amide bond isosteres and/or modification of the native peptide backbone, including chain extension or heteroatom incorporation; examples of which include azapeptides, oligocarbamates, oligoureas, beta-peptides, gamma-peptides, oligo(phenylene ethynylene)s, vinylogous sulfonopeptides, poly-N-substituted glycines (peptoids) and the like. Methods for preparing peptidomimetic compounds are well known in the art and are specified, for example, in Quantitative Drug Design, C.A. Ramsden Gd., Chapter 17.2, F. Choplin Pergamon Press (1992).

As used herein, the term antibody also refers to "non-immunoglobulin agent" as binding agents other than immunoglobulins that are based on different molecular natures, topologies or scaffolds. The term scaffold is meant to describe a protein framework that can carry altered amino acids or sequence insertions that confer on protein variants different functions, usually for binding specific targets. Examples of such non-immunoglobulin agents are well known in the art, and include without limitation peptide aptamers, nucleic acid aptamers, Affibody molecules, Affilins, Affimers, Affitins, Alphabodies, Anticalins, Avimers, DARPins, Fynomers, Kunitz domain peptides Monobodies etc. and other protein scaffolds are reviewed in Binz et al., 2005 (Nat. Biotech. 23:1257-68), and are included herein by reference.

According to the invention the antibodies can be "humanized" to reduce immunogenicity in human individuals. Humanized antibodies improve safety and efficacy of monoclonal antibody therapy. One common method of humanization is to produce a monoclonal antibody in any suitable animal (e.g., mouse, rat, hamster) and replace the constant region with a human constant region, antibodies engineered in this way are termed "chimeric". Another common method is "CDR grafting" which replaces the non-human V-FRs with human V-FRs. In the CDR grafting method all residues except for the CDR region are of human origin.

In another embodiment the inhibitor of expression of CNNM4 is an antagonist. As disclosed herein an "antagonist" is a type of receptor ligand or compound that blocks or dampens a biological response by binding to and blocking a receptor rather than activating it like an agonist. Alternatively, another proteinaceous agent capable of down-regulating the activity of CNNM4 can be a non-functional derivative thereof (i.e. dominant negative). Peptides which mimic these non-functional derivatives and others can be synthesized using solid phase peptide synthesis procedures that are well known in the art and further described by John Morrow Stewart and Janis Dillaha Young, [Solid Phase Peptide Syntheses (2nd Ed., Pierce Chemical Company, 1984)]. Synthetic peptides can be purified by preparative high performance liquid chromatography and the composition of which can be confirmed by amino acid sequencing.

Another class of CNNM4 inhibitors according to the present invention comprises specific soluble binding proteins. These binding proteins do not themselves bind to CNNM4. However, they prevent CNNM4 to interact with effector proteins by complexing the relevant binding site of CNNM4. In another embodiment, said CNNM4-binding inhibitors are soluble receptor variants, which are generated either by proteolytic cleavage of membrane-bound receptors or by translation of alternatively spliced receptor RNAs. Many of these soluble receptors lack a transmembrane and a cytoplasmic domain normally found in membrane-bound forms of the receptor.

In another particular embodiment, the CNNM4 inhibitor is a nucleic acid that specifically binds to the CNNM4 gene or to the transcriptional product of said gene blocking the expression of said gene.

"Nucleic acids" as used herein mean biopolymers of nucleotides, which are linked with one another via phosphodiester bonds (polynucleotides, polynucleic acids). The nucleotides of a nucleic acid may additionally or alternatively be linked via phosphorothioate or phosphorodithionate bonds when chemically synthesized. Depending on the type of sugar in the nucleotides (ribose or deoxyribose), one distinguishes the two classes of the ribonucleic acids (RNA) and the deoxyribonucleic acids (DNA). As used herein it relates to any natural or non-natural nucleic acid and "oligonucleotide" and "polynucleotide" are used interchangeably in the context of the present invention. In the context of the present invention "Natural nucleotides" mean nucleotides that can be purified from natural sources. "Non-natural nucleotides" are defined as those produced using recombinant expression systems and, optionally, purified, chemically synthesized, etc. When appropriate, for example, in the case of chemically synthesized molecules, the nucleic acids can comprise nucleoside analogues such as analogues having chemically modified bases or sugars, modifications of the backbone, etc. A nucleic acid sequence is represented in 5'-3' direction unless indicated otherwise.

In an embodiment the inhibitor of CNNM4 is an antisense polynucleotide. As it is used herein, an "antisense polynucleotide" refers to antisense or sense polynucleotides comprising a single-stranded nucleic acid sequence (RNA or DNA) capable of binding to target mRNA sequences (sense) or DNA sequences (antisense). In a preferred embodiment the antisense polynucleotide is an antisense RNA. In another embodiment the inhibitor of CNNM4 is a RNA interference oligonucleotide.

In another embodiment the inhibitor of CNNM4 is a miRNA. The term "micro RNA" or "miRNA" refers to short single-stranded RNA molecules, typically around 21 to 23 nucleotides long, capable of regulating gene expression. miRNAs may be synthetic (i.e., recombinant) or natural. Natural miRNAs are encoded by genes that are transcribed from DNA and processed from primary transcripts ("pri-miRNA") to short stem-loop structures ("pre-miRNA"), and finally to mature miRNA. Mature miRNA molecules are 5 partially complementary to one or more mRNA molecules, and downregulate gene expression via a process similar to RNA interference, or by inhibiting translation of mRNA.

In another embodiment the inhibitor of CNNM4 is a siRNA. The term "small interfering RNA" ("siRNA") refers to a duplex of small inhibiting RNAs which induce the RNA interference pathway. Small interfering RNAs (siRNAs) are produced in cells by enzymatic cleavage of long dsRNAs by the RNase-III class endoribonuclease Dicer. The siRNAs associate with the RNA Induced Silencing Complex (RISC) in a process that is facilitated by Dicer. Dicer-Substrate RNAi methods take advantage of the link between Dicer and RISC loading that occurs when RNAs are processed by Dicer. Traditional 21-mer siRNAs are chemically synthesized RNA duplexes that mimic Dicer products and bypass the need for Dicer processing. Dicer-Substrate RNAs are chemically synthesized RNA duplexes that are optimized for Dicer processing. These molecules can vary in length (generally from 18 to 30 base pairs) and contain variable degrees of complementarity to their target mRNA in the antisense strand. In a particular embodiment the inhibitor of CNNM4 is a dicer-substrate 27-mer duplex.

Some siRNAs, but not all, have unpaired overhanging bases at the 5' or 3' end of the sense strand and/or the antisense strand. The term "siRNA" includes duplexes of two individual strands. As it is used herein, the siRNA molecules are not limited to RNA molecules but further include nucleic acids with one or more chemically modified nucleotides, such as morpholinos.

In a preferred embodiment, the CNNM4 inhibitor is a siRNA. A siRNA is a nucleic acid that mediates RNA interference (iRNA). In a particular embodiment the siRNA comprises the sequences with SEQ ID NO 13 and SEQ ID NO 14. In another particular embodiment the siRNA comprises any of the sequences SEQ ID NO: 13, SEQ ID NO: 14, SEQ ID NO: 50, or SEQ ID NO: 51. In another particular embodiment, the siRNA comprises a duplex siRNA against human CNNM4, which preferably targets the sequence 5'-GCGAGAGCAUGAAGCUGUAUGCACU-3' (SEQ ID NO 25) (Yamazaki D, et al. (2013), *PLoS Genet* 9(12): e1003983). In further particular embodiments, the siRNA comprises at least one of the sequences with SEQ ID NOs. shown in Table 1. These sequences target either mouse or human CNNM4, as specified, or in some instances both mouse and human CNNM4.

TABLE 1

CNNM4 silencing siRNA sequences.

| SEQUENCE NAME | SEQUENCE | SEQ ID NO. |
|---|---|---|
| Mouse CNNM4 siRNA sequence n1 FW | GAA CUG AGA AGG AGA GAA AUU | SEQ ID NO: 26 |
| Mouse CNNM4 siRNA sequence n1 RV | UUU CUC UCC UUC UCA GUU CUU | SEQ ID NO: 27 |
| Mouse CNNM4 siRNA sequence n2 FW | GGG AGA AGC UGA UGG AGA UUU | SEQ ID NO: 28 |
| Mouse CNNM4 siRNA sequence n2 RV | AUC UCC AUC AGC UUC UCC CUU | SEQ ID NO: 29 |
| Mouse CNNM4 siRNA sequence n3 FW | CAA UGA ACU CAA AGU GAA AUU | SEQ ID NO: 30 |
| Mouse CNNM4 siRNA sequence n3 RV | UUU CAC UUU GAG UUC AUU GUU | SEQ ID NO: 31 |
| Mouse CNNM4 siRNA sequence n4 FW | CGG GAG AAG CUG AUG GAG AUU | SEQ ID NO: 32 |
| Mouse CNNM4 siRNA sequence n4 RV | UCU CCA UCA GCU UCU CCC GUU | SEQ ID NO: 33 |
| Mouse CNNM4 siRNA sequence n5 FW | UGG UGA AGG AGG AGU UAA AUU | SEQ ID NO: 34 |
| Mouse CNNM4 siRNA sequence n5 RV | UUU AAC UCC UCC UUC ACC AUU | SEQ ID NO: 35 |
| Mouse CNNM4 siRNA sequence n6 FW | GUG AAG GAG GAG UUA AAU AUU | SEQ ID NO: 36 |
| Mouse CNNM4 siRNA sequence n6 RV | UAU UUA ACU CCU CCU UCA CUU | SEQ ID NO: 37 |
| Human CNNM4 siRNA sequence n1 FW | GAU UGU AGC UGU UAA GAA AUU | SEQ ID NO: 38 |
| Human CNNM4 siRNA sequence n1 RV | UUU CUU AAC AGC UAC AAU CUU | SEQ ID NO: 39 |
| Human CNNM4 siRNA sequence n2 FW | AGG CAG AGC UCA AGG GAG AUU | SEQ ID NO: 40 |
| Human CNNM4 siRNA sequence n2 RV | UCU CCC UUG AGC UCU GCC UUU | SEQ ID NO: 41 |
| Human CNNM4 siRNA sequence n3 FW | GAU UGU AGC UGU UAA GAA AUU | SEQ ID NO: 42 |
| Human CNNM4 siRNA sequence n3 RV | UUU CUU AAC AGC UAC AAU CUU | SEQ ID NO: 43 |

TABLE 1-continued

CNNM4 silencing siRNA sequences.

| SEQUENCE NAME | SEQUENCE | SEQ ID NO. |
|---|---|---|
| Human CNNM4 siRNA sequence n4 FW | CGA UGG AGA UUU AGA GUA UUU | SEQ ID NO: 44 |
| Human CNNM4 siRNA sequence n4 RV | AUA CUC UAA AUC UCC AUC GUU | SEQ ID NO: 45 |
| Human CNNM4 siRNA sequence n5 FW | GCU GAU GAG UGC AAA GAA AUU | SEQ ID NO: 46 |
| Human CNNM4 siRNA sequence n5 RV | UUU CUU UGC ACU CAU CAG CUU | SEQ ID NO: 47 |
| Human CNNM4 siRNA sequence n6 FW | CCU CAA AGC UCA AGG CAC AUU | SEQ ID NO: 48 |
| Human CNNM4 siRNA sequence n6 RV | UGU GCC UUG AGC UUU GAG GUU | SEQ ID NO: 49 |

In another embodiment the inhibitor of CNNM4 is a shRNA. As it is used herein, the term "shRNA" or "short hairpin RNA" refers to a double stranded RNA (dsRNA) where the two strands are bound by a strand without interrupting the nucleotides between 5 the 3' end of one strand and the 5' end of the other respective strand to form a duplex structure. shRNAs can be used to silence a target gene expression via RNA interference since, once the shRNA is processed is located to the RNA-induced silencing complex (RISC), targeting RISC to an mRNA that has a complementary sequence. RISC may cleave this mRNA or repress its translation. In a particular embodiment the shRNA comprises the sequence with SEQ ID NO 52.

In another embodiment the inhibitor of CNNM4 is a sgRNA. As disclosed herein the term single guide RNA ("sgRNA") refers to a chimeric non-coding RNA that contains a targeting sequence (crRNA sequence), that specifically recognizes a region of a gene, and a CRISPR enzyme. The crRNA region is a 20-nucleotide sequence that is homologous to a region in the gene of interest and will direct the CRISPR enzyme activity. As disclosed herein, a CRISPR enzyme can be any known in the art, such as Cas9 and Cpf1.

As disclosed herein, CRISPR is a genome editing method. The use of this technology in genome editing is well described in the art, for example in U.S. Pat. No. 8,697,359 and references cited herein. In short, CRISPR is a microbial nuclease system involved in defense against invading phages and plasmids. CRISPR loci in microbial hosts contain a combination of CRISPR-associated (Cas) genes as well as non-coding RNA elements capable of programming the specificity of the CRISPR-mediated nucleic acid cleavage (sgRNA). Three types (I-III) of CRISPR systems have been identified across a wide range of bacterial hosts. One key feature of each CRISPR locus is the presence of an array of repetitive sequences (direct repeats) interspaced by short stretches of non-repetitive sequences (spacers). The non-coding CRISPR array is transcribed and cleaved within direct repeats into short crRNAs containing individual spacer sequences, which direct Cas nucleases to the target site (protospacer). The Type II CRISPR is one of the better-characterized systems and carries out targeted DNA double-strand break in four sequential steps. First, two noncoding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer.

One major advantage of the CRISPR-Cas9 system, as compared to conventional gene targeting and other programmable endonucleases is the ease of multiplexing, where multiple genes can be mutated simultaneously simply by using multiple sgRNAs each targeting a different gene. In addition, where two sgRNAs are used flanking a genomic region, the intervening section can be deleted or inverted.

Cas9 is thus the hallmark protein of the type II CRISPR-Cas system, and is a large monomeric DNA nuclease guided to a DNA target sequence adjacent to the PAM (protospacer adjacent motif) sequence motif by a complex of two non-coding RNAs: CRISPR RNA (crRNA) and trans-activating crRNA (tracrRNA). The Cas9 protein contains two nuclease domains homologous to RuvC and HNH nucleases. The HNH nuclease domain cleaves the complementary DNA strand whereas the RuvC-like domain cleaves the non-complementary strand and, as a result, a blunt cut is introduced in the target DNA. Heterologous expression of Cas9 together with a sgRNA can introduce site-specific double strand breaks (DSBs) into genomic DNA of live cells from various organisms. For applications in eukaryotic organisms, codon optimized versions of Cas9, which is originally from the bacterium *Streptococcus pyogenes*, have been used, although other suitable Cas9 orthologues can be used instead, such as *Staphylococcus aureus* Cas9 (SaCas9), *Campylobacter jejuni* Cas9 (CjCas9).

The single guide RNA (sgRNA) is the second component of the CRISPR/Cas system that forms a complex with the Cas9 nuclease. sgRNA is a synthetic RNA chimera created by fusing crRNA with tracrRNA. The sgRNA guide sequence located at its 5' end confers DNA target specificity. Therefore, by modifying the guide sequence, it is possible to create sgRNAs with different target specificities. The canonical length of the guide sequence is 20 bp. In plants, sgRNAs have been expressed using plant RNA polymerase III promoters, such as U6 and U3.

Cas9 expression plasmids for use in the methods of the invention can be constructed as described in the art.

By "crRNA" or CRISPR RNA is meant the sequence of RNA that contains the protospacer element and additional nucleotides that are complementary to the tracrRNA.

By "tracrRNA" (transactivating RNA) is meant the sequence of RNA that hybridises to the crRNA and binds a CRISPR enzyme, such as Cas9 thereby activating the nuclease complex to introduce double-stranded breaks at specific sites within the genomic sequence of at least one of the alpha-, gamma- and/or omega gliadin.

By "protospacer element" is meant the portion of crRNA (or sgRNA) that is complementary to the genomic DNA target sequence, usually around 20 nucleotides in length. This may also be known as a spacer or targeting sequence.

By "sgRNA" (single-guide RNA) is meant the combination of tracrRNA and crRNA in a single RNA molecule, preferably also including a linker loop (that links the tracrRNA and crRNA into a single molecule). "sgRNA" may also be referred to as "gRNA" and in the present context, the terms are interchangeable. The sgRNA or gRNA provide both targeting specificity and scaffolding/binding ability for a Cas nuclease. A gRNA may refer to a dual RNA molecule comprising a crRNA molecule and a tracrRNA molecule. A sgRNA can be provided as an RNA molecule or as a DNA molecule that is transcribed into the functional sgRNA.

By "CRISPR enzyme" is meant an RNA-guided DNA endonuclease that can associate with the CRISPR system. Specifically, such an enzyme binds to the tracrRNA sequence. In one embodiment, the CRIPSR enzyme is a Cas protein ("CRISPR associated protein), preferably Cas9 or Cpf1.

In another embodiment the inhibitor of CNNM4 is an aptamer. As it is used herein, the term "aptamer" means oligonucleotides that selectively bind a target ligand, but do not catalyze a subsequent chemical reaction. The term "peptide aptamer" refers to a short variable peptide domain that is attached at both ends to a protein scaffold, and that binds to a specific target molecule. The variable loop length is typically composed of ten to twenty amino acids, and the scaffold may be any protein which has good solubility and compacity properties. The term "nucleic acid aptamer" or "DNA aptamer", as used herein, refers to a short strand of DNA that has been engineered through repeated rounds of selection to bind to specific molecular targets.

In another embodiment the inhibitor of CNNM4 is a DNAzyme. As it is used herein, the term "DNAzyme", refers to DNA oligonucleotides that are capable of performing a specific chemical reaction, usually catalytic.

In another embodiment the inhibitor of CNNM4 is a ribozyme. As it is used herein, the term "ribozyme" or "RNA enzyme" or "catalytic RNA" refers to an RNA molecule which catalyzes a chemical reaction. Ribozymes may be used to hydrolyse phosphodiester bonds in other RNAs. The nucleic acid with the capacity to inhibit the expression of CNNM4 may contain one or more modifications in the nucleobases, in the sugars, and/or in the bonds between nucleotides.

In another embodiment the inhibitor of CNNM4 is a triplex forming oligonucleotide. As it is used herein, the term "triplex forming oligonucleotide (TFO)", are oligonucleotides able to form a triplex which binds in the major groove of duplex DNA in a sequence-specific manner through the formation of hydrogen bonds. All inhibitors previously described may be subject to one or more modifications. Modifications to one or more residues of the nucleic acid backbone may comprise one or more of the following: modifications of the sugar at 2' such as 2'-O-methyl (2'-OMe), 2'-O-methoxyethyl (2'-MOE), 2'-O-methoxyethoxy, 2'-fluoro (2'-F), 2'-allyl, 2'-O-[2-(methyl-amino)-2-oxoethyl], 2'-O—(N-methylcarbamate); modifications of the sugar at 4' including 4'-thio, 4'-CH2-O-2' bridge, 4-(CH2)2-O-2' bridge; locked nucleic acid (LNA); peptide nucleic acid (PNA); intercalating nucleic acid (INA); twisted intercalating nucleic acid (TINA); hexitol nucleic acids (HNA); arabinonucleic acid (ANA); cyclohexene nucleic acids (CNAs); cyclohexenyl nucleic acid (CeNA); threose nucleic acid (TNA); morpholine oligonucleotides; Gapmers; Mixmers; incorporation of arginine-rich peptides; addition of 5'-phosphate to synthetic RNAs; RNA aptamers (Que-Gewirth N S, Gene Ther. 2007 February; 14(4):283-91.); antidote-controlled RNA aptamers in the subject of the specific RNA aptamer (ref. Oney S, Oligonucleotides. 2007 Fall; 17(3):265-74), or any combination thereof.

Modifications to one or more nucleoside bonds of the nucleic acids may comprise one or more of the following: phosphorothioate, phosphorodithioate, phosphoramidate, phosphorodiamidate, phosphorodithioate, phosphoroselenoate, phosphorodiselenoate, phosphoroanilothioate, and phosphoroanilidate, or any combination thereof.

A locked nucleic acid (LNA), commonly referred to as inaccessible RNA, is a modified RNA nucleotide. The ribose group of an LNA nucleotide is modified with an extra bridge joining carbons 2' and 4' (O2', C4'-methylene bridge). The bridge "locks" the ribose in the 3'-endo structural conformation, which is usually found in the A form of DNA or RNA. LNA nucleotides can be mixed with DNA or RNA bases in the nucleic acid when desired. Such oligomers are commercially available.

A peptide nucleic acid (PNA) is an artificially synthesized polymer the backbone of which is made up of repeating units of N-(2-aminoethyl)-glycine linked by peptide bonds. The different purine and pyrimidine bases are linked to the backbone by methylene-carbonyl bonds.

An intercalating nucleic acid (INA) is a modified nucleic acid analogue comprising normal deoxyribonucleotides covalently bound to hydrophobic insertions.

Hexitol nucleic acids (HNAs) are nucleotides formed by natural nucleobases and a phosphorylated 1,5-anhydrohexitol backbone. The molecular associations between HNA and RNA are more stable than that between HNA and DNA and between natural nucleic acids (dsDNA, dsRNA, DNA/RNA). Other synthetically modified oligonucleotides comprise ANA (arabinonucleic acid), CNAs (cyclohexene nucleic acids), CeNA (cyclohenexyl nucleic acid), and TNA (threose nucleic acid).

Morpholinos are synthetic molecules which are the product of redesigning the natural nucleic acid structure. Structurally, the difference between morpholinos and DNA or RNA is that while morpholinos have standard nucleobases, those bases are linked to 6-membered morpholine rings instead of to deoxyribose/ribose rings, and the non-ionic phosphorodiamidate bonds between the subunits replace the anionic phosphodiester bonds. Morpholinos are sometimes referred to as PMO (phosphorodiamidate morpholino oligonucleotide). The 6 membered morpholine ring has the chemical formula O (CH2 CH2)2 NH.

Gapmers or "oligomeric compounds with gaps" are RNA-DNA-RNA chimeric oligonucleotide probes, where DNA windows or gaps are inserted in either a normal or modified RNA oligonucleotide known as "wings". This modification increases the stability of the oligonucleotide in vivo and makes the probe more prone to interacting with the target, such that shorter probes can be effectively used. Preferably, the wings are modified 2'-O-methyl (OMe) or 2'-O-methoxyethyl (MOE) oligonucleotides which protect the internal block from nuclease degradation. Furthermore, the nucleotides forming the gap or wings can be linked by phosphodiester bonds or by phosphorothioate bonds, which thereby makes them resistant to RNAse degradation. Furthermore, the nucleotides forming the wings can also be modified by the incorporation of bases linked by 3'-methylphosphonate bonds.

In another embodiment the inhibitor of CNNM4 is a small molecule. As it is used herein, the term "small molecule" refers to a low molecular weight (<900 daltons) organic compound that is capable of regulating a biological process. Small molecules are capable of inhibiting a specific function of a protein or disrupting protein-protein interactions. In a preferred embodiment the small molecule is 7-amino-2-phenyl-5H-thieno[3,2-c]pyridin-4-one (PubChem CID 91383855) or the rhodanine derivative known as 2-[5-(4-Oxo-2-thioxo-thiazolidin-5-ylidenemethyl)-furan-2-yl]-benzoic acid as described in Park, H., et al. 2008. *Bioorg Med Chem Lett*. 18(7):2250-5 (Chemspider ID 1014170).

In another embodiment the inhibitor of CNNM4 is any combination of the aforementioned inhibitors.

As used herein, the terms "treatment," "treating," and the like, comprises any type of therapy, which aims at terminating, preventing, ameliorating and/or reducing the susceptibility to a clinical condition as described herein. Thus, "treatment" "treating" and the like, as used herein, refer to obtaining a desired pharmacologic and/or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse effect attributable to the disorder. It covers any treatment of a disease in a mammal, particularly in a human, and includes: (a) increasing survival time; (b) decreasing the risk of death due to the disease; (c) preventing the disease from occurring in a subject which may be predisposed to the disease but has not yet been diagnosed as having it; (d) inhibiting the disease, i.e., arresting its development (e.g., reducing the rate of disease progression); and (e) relieving the disease, i.e., causing regression of the disease.

As used herein, "disease" means a condition of the living animal or of one of its parts that impairs normal functioning and is typically manifested by distinguishing signs and symptoms. Animals of preferred embodiments are mammals, preferably humans.

As used herein, "acute disease" means a condition which is severe and sudden in onset.

As used herein, "chronic disease" means a condition which is long-developing. Acute diseases may lead to chronic diseases.

The terms "subject", "patient" or "individual" are used herein interchangeably to refer to any member of the animal kingdom and can be a vertebrate, such as a mammal, a fish, a bird, a reptile, or an amphibian, including a human, non-human primate, horse, pig, rabbit, dog, sheep, goat, cow, cat, guinea pig or rodent. Preferably, the subject is mammal, more preferably a human.

According to the invention, the disease is selected from the group consisting of a liver disease, a kidney disease and a lung disease. In one embodiment, the disease is a non-proliferative disease (i.e., the disease is a disease other than cancer).

As used herein, a "liver disease" is an acute or chronic damage to the liver, usually caused by infection, injury, exposure to drugs or toxic compounds, alcohol, impurities in foods, and the abnormal build-up of normal substances in the blood, an autoimmune process, or by a genetic defect (such as haemochromatosis). Sometimes the exact cause of the injury may not be known. Liver disease can be classified as acute or chronic liver disease based in the duration of the disease. In acute liver disease, such as acute hepatitis and acute liver failure (ALF), the history of the disease does not exceed six months. Liver diseases of longer duration are classified as chronic liver disease. Non-limiting examples of common liver diseases include cirrhosis, liver fibrosis, non-alcoholic fatty liver disease (NAFLD), non-alcoholic steatohepatitis (NASH), hepatic ischemia reperfusion injury, primary biliary cirrhosis (PBC), and hepatitis, including viral and alcoholic hepatitis. Most common forms of viral hepatitis are hepatitis B and C (HBV and HCV, respectively). Chronic hepatitis may result in cirrhosis. The death of liver cells through a process known as apoptosis is common in all forms of liver disease. Apoptosis of liver cells is linked to liver fibrosis and other liver disease.

Liver disease and, in particular, liver disease caused by drugs (drug-induced liver injury or DILI), manifests itself clinically in a variety of symptoms which as such are not particular informative. Non-limiting examples of symptoms include: loss of appetite, exhaustion, giddiness, weight loss, nausea, vomiting, fever, pain in the upper right abdominal region, arthralgias, myalgias, itching, rashes, discoloration of excretions may be mentioned, yellowing of the eyes and of the skin.

As an expert in the field knows, the presence of active liver disease is often detected by the existence of elevated enzyme levels in the blood. Specifically, blood levels of ALT (alanine aminotransferase) and AST (aspartate aminotransferase) above clinically accepted normal ranges are known to be indicative of on-going liver damage. Routine monitoring of liver disease patients for blood levels of ALT and AST is used clinically to measure progress of the liver disease while on medical treatment. Reduction of elevated ALT and AST to within the accepted normal range is taken as clinical evidence reflecting a reduction in the severity of the patient on-going liver damage. In a particular embodiment, the liver disease is caused by any kind of liver damage.

The term "liver damage", as used herein, is used to denote any type of hepatic trauma (injury), including chronic and acute trauma as well as pathological change present in liver cell or tissue. The clinical conditions of liver damage may include, without being limited thereto, degeneration of live cells, vasculitis of liver, spotty necrosis or focal necrosis present in liver, inflammatory cell infiltration or fibroblast proliferation in liver and portal area, or hepatomegaly, and hepatocirrhosis, hepatoma resulted from severe liver damage, and the like. Liver disease results from an injury to the liver. The injury to the liver may be caused by toxins, including alcohol, some drugs, impurities in foods, the abnormal build-up of normal substances in the blood, by infection or by an autoimmune disorder. In some cases, the liver damage resulting from an injury to the liver include, but is not limited to fatty liver, cirrhosis, primary biliary cirrhosis, primary sclerosing cholangitis, and alpha1-antitrypsin deficiency. The liver damage includes, but is not limited to cirrhosis, liver fibrosis, non-alcoholic fatty liver disease (NAFLD), non-alcoholic steatohepatitis (NASH), hepatic ischemia reperfusion injury, hepatitis, including viral and alcoholic hepatitis and primary biliary cirrhosis (PBC).

In a preferred embodiment, the liver disease is selected from liver fibrosis, veno-occlusive liver disease, drug-induced liver injury (DILI), steatosis, non-alcoholic steatohepatitis (NASH), cirrhosis, hepatocellular carcinoma (HCC), Budd-Chiari syndrome and hepatitis, or any combination thereof. In a more preferred embodiment, the liver disease is selected from liver fibrosis, veno-occlusive liver disease, drug-induced liver injury (DILI), non-alcoholic steatohepatitis (NASH), cirrhosis, hepatocellular carcinoma (HCC), Budd-Chiari syndrome and hepatitis, or any combination thereof. In a more preferred embodiment, the liver disease is selected from drug-induced liver injury (DILI), non-alcoholic steatohepatitis (NASH), cirrhosis, hepatocellular carcinoma (HCC) or any combination thereof. In a more preferred embodiment, the liver disease is selected from drug-induced liver injury (DILI), non-alcoholic steatohepatitis (NASH), cirrhosis or any combination thereof.

As used herein, "fibrosis" is the formation of excess fibrous connective tissue in an organ or tissue in a reparative or reactive process. This can be a reactive, benign, or pathological state. In response to injury, this is called scarring, and if fibrosis arises from a single cell line, this is called a fibroma. Physiologically, fibrosis acts to deposit connective tissue, which can interfere with or totally inhibit the normal architecture and function of the underlying organ or tissue. Fibrosis can be used to describe the pathological state of excess deposition of fibrous tissue, as well as the process of connective tissue deposition in healing. Defined by the pathological accumulation of extracellular matrix (ECM) proteins, fibrosis results in scarring and thickening of the affected tissue, it is in essence an exaggerated wound healing response which interferes with normal organ function. Fibrosis may affect any organ. In a preferred embodiment, fibrosis is liver fibrosis.

As used herein "liver fibrosis" is the scarring process that represents the liver's response to injury. In the same way as skin and other organs heal wounds through deposition of collagen and other matrix constituents so the liver repairs injury through the deposition of new collagen. Liver fibrosis is the first stage of liver scarring. Later, if more of the liver becomes scarred, it may lead to liver cirrhosis.

As used herein "veno-occlusive liver disease" or "hepatic sinusoidal obstruction syndrome (SOS)" is characterized by hepatomegaly, right upper quadrant pain, jaundice, and ascites, most often occurring in patients undergoing hematopoietic cell transplantation (HCT) and less commonly following the use of certain chemotherapeutic agents in non-transplant settings, ingestion of alkaloid toxins, after high dose radiation therapy, or liver transplantation. The hepatic venous outflow obstruction in SOS is due to occlusion of the terminal hepatic venules and hepatic sinusoids.

As used herein "drug-induced liver injury (DILI)" means injury to the liver developed following the use of one or more drugs.

As used herein "steatosis", also called fatty change, is the process describing the abnormal retention of lipids within a cell. It reflects an impairment of the normal processes of synthesis and elimination of triglyceride fat. Excess lipid accumulates in vesicles that displace the cytoplasm. When the vesicles are large enough to distort the nucleus, the condition is known as macrovesicular steatosis; otherwise, the condition is known as microvesicular steatosis. While not particularly detrimental to the cell in mild cases, large accumulations can disrupt cell constituents, and in severe cases the cell may even burst. The risk factors associated with steatosis are varied, and include diabetes mellitus, protein malnutrition, hypertension, cell toxins, obesity, anoxia, and sleep apnea. As the liver is the primary organ of lipid metabolism it is most often associated with steatosis; however, it may occur in any organ, commonly the kidneys, heart, and muscle. In a preferred embodiment, the steatosis is caused in the liver.

As used herein "non-alcoholic steatohepatitis (NASH)" is a syndrome that develops in patients who are not alcoholic; it causes liver damage that is histologically indistinguishable from alcoholic hepatitis. It develops most often in patients with at least one of the following risk factors: obesity, dyslipidemia, and glucose intolerance. Pathogenesis is poorly understood but seems to be linked to insulin resistance (eg, as in obesity or metabolic syndrome). Most patients are asymptomatic. Laboratory findings include elevations in aminotransferase levels. Biopsy is required to confirm the diagnosis.

As used herein "cirrhosis", means a late stage of progressive hepatic fibrosis characterized by distortion of the hepatic architecture and the formation of regenerative nodules. It is generally considered to be irreversible in its advanced stages, at which point the only treatment option may be liver transplantation. Reversal of cirrhosis (in its earlier stages) is possible in several forms of liver disease following treatment of the underlying cause. Patients with cirrhosis are susceptible to a variety of complications, and their life expectancy is usually markedly reduced.

As used herein "hepatocellular carcinoma (HCC)", means an aggressive tumour that often occurs in the setting of chronic liver disease and cirrhosis. It is typically diagnosed late in its course, and the median survival following diagnosis is approximately 6 to 20 months. Although the mainstay of therapy is surgical resection, the majority of patients are not eligible because of tumour extent or underlying liver dysfunction.

As used herein "Budd-Chiari syndrome" (BCS) is defined as hepatic venous outflow tract obstruction, independent of the level or mechanism of obstruction, provided the obstruction is not due to cardiac disease, pericardial disease, or sinusoidal obstruction syndrome (veno-occlusive disease). Primary Budd-Chiari syndrome is present when there is obstruction due to a predominantly venous process (thrombosis or phlebitis), whereas secondary Budd-Chiari is present when there is compression or invasion of the hepatic veins and/or the inferior vena cava by a lesion that originates outside of the vein (eg, a malignancy).

As used herein "hepatitis" means an inflammation of the liver, irrespective of the cause. Hepatitis may be caused by a number of conditions, including drug toxicity, immune diseases, and viruses. It is characterized by jaundice, liver enlargement, and fever.

As used herein, a "kidney disease" is an acute or chronic damage to the kidney. It refers to a disease occurring in kidneys due to various reasons including extrinsic factors, intrinsic factors, genetic factors, etc. Non-limiting examples of the renal disease include: nephritis, nephrosis, renal fibrosis, thin glomerular basement membrane (TGBM), minimal change disease (MCD), membranous glomerulonephritis (MGN), focal segmental glomerulosclerosis (FSGS), DM nephropathy, IgA nephropathy (IgAN), tubulointerstitial nephritis (TIN), Henoch-Schonlein Purpura (HSP) nephritis, acute tubular injury, BK virus nephropathy, acute cellular rejection, chronic antibody mediated rejection, chronic active antibody mediated rejection, chronic calcineurin inhibitor toxicity, acute kidney injury, chronic kidney disease, ischemic renal disease, glomerulonephritis, lupus nephritis, polycystic kidney disease, pyelonephritis, nephrolith, renal tuberculosis, renal tumor, chronic renal failure, end stage renal failure, sepsis, renal injury caused by hepatic injury, etc.

In a preferred embodiment, the kidney disease is selected from acute kidney injury (AKI), chronic kidney disease, nephritis, nephrosis and renal fibrosis.

As used herein "acute kidney injury (AKI)" or "acute renal failure (ARF)" is an abrupt loss of kidney function that develops within 7 days. Non-limiting causes include: damage to the kidney tissue caused by decreased kidney blood flow (kidney ischemia) from any cause (e.g., low blood pressure), exposure to substances harmful to the kidney, an inflammatory process in the kidney, or an obstruction of the urinary tract that impedes the flow of urine. AKI is diagnosed on the basis of characteristic laboratory findings, such as elevated blood urea nitrogen and creatinine, or inability of the kidneys to produce sufficient amounts of urine. AKI may lead to a number of complications, including metabolic acidosis, high potassium levels, uremia, changes in body fluid balance, and effects on other organ systems, including death. People who have experienced AKI may have an increased risk of chronic kidney disease in the future.

As used herein "chronic kidney disease (CDK)" means a type of kidney disease in which there is gradual loss of kidney function over a period of months or years. Early on there are typically no symptoms. Later, leg swelling, feeling tired, vomiting, loss of appetite, or confusion may develop. Complications may include heart disease, high blood pressure, bone disease, or anemia. Non-limiting causes of chronic kidney disease include diabetes, high blood pressure, glomerulonephritis, and polycystic kidney disease. Risk factors include a family history of the condition. Diagnosis is generally by blood tests to measure the glomerular filtration rate and urine tests to measure albumin. Further tests such as an ultrasound or kidney biopsy may be done to determine the underlying cause.

As used herein "nephritis" means an inflammation of the kidneys and may involve the glomeruli, tubules, or interstitial tissue surrounding the glomeruli and tubules. Non-limiting causes include: infections, toxins and autoimmune disorders. Nephritis includes glomerulonephritis (inflammation of the glomeruli) and interstitial nephritis or tubulointerstitial nephritis (inflammation of the spaces between renal tubules).

As used herein "nephrosis" means any degenerative disease of the kidney tubules. Nephrosis can be caused by kidney disease, or it may be a complication of another disorder, particularly diabetes. Diagnosis is made via urine testing for the presence of protein, blood testing for lower-than-normal levels of protein, and observation of edema.

In a preferred embodiment, fibrosis is renal fibrosis. As used herein "renal fibrosis" means fibrosis affecting the kidneys.

As used herein a "respiratory disease" means any pathological condition affecting the organs and tissues that make gas exchange possible in higher organisms, and includes conditions of the upper respiratory tract, trachea, bronchi, bronchioles, alveoli, pleura and pleural cavity, and the nerves and muscles of breathing.

As used herein, a "lung disease" is any respiratory disease affecting the lungs. A lung disease may be an acute or chronic damage to the lung. Non-limiting examples of lung diseases include: asthma, chronic obstructive pulmonary disease, chronic or acute bronchitis, cystic fibrosis emphysema, acute respiratory distress syndrome, bacterial pneumonia, tuberculosis pulmonary embolism and lung cancer.

In a preferred embodiment, the lung disease is pulmonary fibrosis. As used herein, "pulmonary fibrosis" means a respiratory disease in which scars are formed in the lung tissues, leading to breathing problems. Scar formation, the accumulation of excess fibrous connective tissue (the process called fibrosis), leads to thickening of the walls, and causes reduced oxygen supply in the blood. As a consequence patients may suffer from shortness of breath. Symptoms of pulmonary fibrosis include: shortness of breath, chronic dry, hacking coughing, fatigue and weakness, chest discomfort including chest pain, loss of appetite and rapid weight loss. As disclosed herein, pulmonary fibrosis may be a secondary effect of other diseases and/or of specific treatments comprising a non-invasive administration for systemic and local delivery of therapeutic agents to the lungs, such as intranasal administration and oral inhalative administration. Non-liming examples of diseases and conditions that may cause pulmonary fibrosis as a secondary effect include: inhalation of environmental and occupational pollutants, such as metals in asbestosis, silicosis and exposure to certain gases; hypersensitivity pneumonitis, most often resulting from inhaling dust contaminated with bacterial, fungal, or animal products; cigarette smoking; some connective tissue diseases such as rheumatoid arthritis, Systemic lupus erythematosus (SLE) and scleroderma, sarcoidosis and granulomatosis with polyangiitis; infections; certain medications, e.g. amiodarone, bleomycin (pingyangmycin), busulfan, methotrexate, apomorphine and nitrofurantoin; radiation therapy to the chest.

In a particular embodiment the CNNM4 inhibitor for the use of the invention can be administered forming part of a pharmaceutical composition, wherein the CNNM4 inhibitor is administered together with a pharmaceutically acceptable excipient. Accordingly, the invention refers to a pharmaceutical composition comprising a CNNM4 inhibitor as described herein and a pharmaceutically acceptable excipient, for use in medicine (i.e. as a treatment). The invention further refers to a pharmaceutical composition comprising a CNNM4 inhibitor as described herein and a pharmaceutically acceptable excipient, for use in the treatment of an acute or a chronic disease in a subject, wherein the disease is preferably selected from the group consisting of a liver disease, a kidney disease and a lung disease.

A "pharmaceutical composition" as used herein, relates to compositions and molecular entities that are physiologically tolerable and do not typically produce an allergic reaction or a similar unfavourable reaction as gastric disorders, dizziness and suchlike, when administered to a human or animal. Preferably, the term "pharmaceutically acceptable" means it is approved by a regulatory agency of a state or federal government or is included in the U.S. Pharmacopoeia or other generally recognized pharmacopoeia for use in animals, and more particularly in humans.

The term "excipient" refers to a vehicle, diluent or adjuvant that is administered with the active ingredient. Such pharmaceutical excipients can be sterile liquids, such as water and oils, including those of petroleum, animal, vegetable or synthetic origin, such as peanut oil, soybean oil, mineral oil, sesame oil and similar. Water or saline aqueous solutions and aqueous dextrose and glycerol solutions, particularly for injectable solutions, are preferably used as vehicles. Suitable pharmaceutical vehicles are described in "Remington's Pharmaceutical Sciences" by E. W. Martin, $21^{st}$ Edition, 2005; or "Handbook of Pharmaceutical Excipients", Rowe C. R.; Paul J. S.; Marian E. Q., sixth Edition.

Appropriate amounts of an inhibitor as defined above can be formulated with pharmaceutically acceptable excipients and/or carriers to obtain a pharmaceutical composition for use in medicine, particularly for use in the treatment of a liver disease, a kidney disease and/or a lung disease.

Suitable pharmaceutically acceptable vehicles include, for example, water, salt solutions, alcohol, vegetable oils, polyethylene glycols, gelatin, lactose, amylose, magnesium stearate, talc, surfactants, silicic acid, viscous paraffin, perfume oil, monoglycerides and diglycerides of fatty acids, fatty acid esters petroetrals, hydroxymethyl cellulose, polyvinylpyrrolidone and the like.

The pharmaceutical composition comprising the inhibitor as defined above can occur at any pharmaceutical form of administration considered appropriate for the selected administration route, for example, by systemic (e.g. intravenous, subcutaneous, intramuscular injection), oral, parenteral or topical administration, for which it will include the pharmaceutically acceptable excipients necessary for formulation of the desired method of administration. Additionally, it is also possible to administer the composition comprising the inhibitor as defined above intranasally or sublingually which allows systemic administration by a non-aggressive mode of administration. Intraventricular administration may be also adequate. In a preferred embodiment, the route of administration is an intravenous route. In an alternative preferred embodiment, the route of administration is a subcutaneous route.

Where necessary, the inhibitor for the use of the invention is comprised in a composition also including a solubilizing agent and a local anaesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

In cases other than intravenous administration, the composition can contain minor amounts of wetting or emulsifying agents, or pH buffering agents. The composition can be a liquid solution, suspension, emulsion, gel, polymer, or sustained release formulation. The composition can be formulated with traditional binders and carriers, as would be known in the art. Formulations can include standard carriers such as pharmaceutical grades of mannitol, lactose, starch, magnesium stearate, sodium saccharide, cellulose, magnesium carbonate, etc., inert carriers having well established functionality in the manufacture of pharmaceuticals. Various delivery systems are known and can be used to administer a therapeutic of the present invention including encapsulation in liposomes, microparticles, microcapsules and the like.

Solid dosage forms for oral administration may include conventional capsules, sustained release capsules, conventional tablets, sustained-release tablets, chewable tablets, sublingual tablets, effervescent tablets, pills, suspensions, powders, granules and gels. At these solid dosage forms, the active compounds can be mixed with at least one inert excipient such as sucrose, lactose or starch. Such dosage forms can also comprise, as in normal practice, additional substances other than inert diluents, e.g. lubricating agents such as magnesium stearate. In the case of capsules, tablets, effervescent tablets and pills, the dosage forms may also comprise buffering agents. Tablets and pills can be prepared with enteric coatings.

Liquid dosage forms for oral administration may include emulsions, solutions, suspensions, syrups and elixirs pharmaceutically acceptable containing inert diluents commonly used in the technique, such as water. Those compositions may also comprise adjuvants such as wetting agents, emulsifying and suspending agents, and sweetening agents, flavouring and perfuming agents.

Injectable preparations, for example, aqueous or oleaginous suspensions, sterile injectable may be formulated according with the technique known using suitable dispersing agents, wetting agents and/or suspending agents. Among the acceptable vehicles and solvents that can be used are water, Ringer's solution and isotonic sodium chloride solution. Sterile oils are also conventionally used as solvents or suspending media.

For topical administration, compounds of the invention can be formulated as creams, gels, lotions, liquids, pomades, spray solutions, dispersions, solid bars, emulsions, microemulsions and similar which may be formulated according to conventional methods that use suitable excipients, such as, for example, emulsifiers, surfactants, thickening agents, colouring agents and combinations of two or more thereof.

Additionally, the inhibitor as defined above may be administered in the form of transdermal patches or iontophoresis devices. Suitable transdermal patches are known in the art.

Several drug delivery systems are known and can be used to administer the inhibitor as defined above, including, for example, encapsulation in liposomes, microbubbles, emulsions, microparticles, microcapsules, cationic lipids and similar. Cationic lipids, also called "bolaamphiphiles" or "bolas", consist of a hydrophobic chain with one or more positively charged head groups at each end. The required dosage can be administered as a single unit or in a sustained release form. Non-limiting examples of non-invasive specific treatments include: the use of viral vectors for airway gene delivery to the lungs, such as lentiviruses and adenoviruses, and nanotechnologies based on polymers, which can also be locally administered to the lungs by inhalation. The way of administration can be any technique known in the art, such as those using any of the devices most commonly used for respiratory delivery, including nebulizers, metered-dose inhalers, and dry powder inhalers.

Sustainable-release forms and appropriate materials and methods for their preparation are described in, for example, "Modified-Release Drug Delivery Technology", Rathbone, M. J. Hadgraft, J. and Roberts, M. S. (eds.), Marcel Dekker, Inc., New York (2002), "Handbook of Pharmaceutical Controlled Release Technology", Wise, D. L. (ed.), Marcel Dekker, Inc. New York, (2000). In one embodiment of the invention, the orally administrable form of an inhibitor according to the invention is in a sustained release form further comprises at least one coating or matrix. The coating or sustained release matrix include, without limitation, natural polymers, semisynthetic or synthetic water-insoluble, modified, waxes, fats, fatty alcohols, fatty acids, natural semisynthetic or synthetic plasticizers, or a combination of two or more of the them. Enteric coatings may be applied using conventional processes known to experts in the art, as described in, for example, Johnson, J. L., "Pharmaceutical tablet coating", Coatings Technology Handbook (Second Edition), Satas, D. and Tracton, A. A. (eds), Marcel Dekker, Inc. New York, (2001), Carstensen, T., "Coating Tablets in Advanced Pharmaceutical Solids", Swarbrick, J. (ed.), Marcel Dekker, Inc. New York (2001), 455-468.

In an embodiment the CNNM4 inhibitor is a siRNA. Methods for in vivo delivery of siRNA are known in the art (Davis, M. E. et al., *Nature* 2010 April 15; 464(7291): 1067-1070).

In an embodiment, the siRNA is conjugated to at least one ligand. The ligand is preferably specific for a receptor expressed on the surface of a target cell. For siRNAs that are to be targeted to hepatocytes, the at least one ligand is preferably a GalNAc or a GalNAc derivative.

In a particular embodiment, siRNA is used at a concentration of between 0.1 µg/µl and 2.5 µg/ml. In a preferred embodiment, siRNA is used at a concentration of at least 0.1 µg/µl, at least 0.2 µg/µl, at least 0.3 µg/µl, at least 0.4 µg/µl, at least 0.5 µg/µl, at least 0.6 µg/µl, at least 0.7 µg/µl, at least 0.8 µg/µl, at least 0.9 µg/µl, at least 1 µg/µl, at least, 1.1 µg/µl, at least 1.2 µg/µl, at least 1.3 µg/µl, at least 1.4 µg/µl, at least 1.5 µg/µl, at least 1.6 µg/µl, at least 1.7 µg/µl, at least 1.8 µg/µl, at least 1.9 µg/µl, at least 2 µg/µl, least 2.1 µg/µl, at least 2.2 µg/µl, at least 2.3 µg/µl, at least 2.4 µg/µl, at least 2.5 µg/µl, or more. In another preferred embodiment, siRNA is used at a concentration of 0.75 µg/µl.

In a particular embodiment, siRNA is used at a dose of between 0.1 and 10 mg per kilogram of patient. In a preferred embodiment, siRNA is used at a dose of at least 0.1 mg/kg, at least 0.5 mg/kg, at least 1 mg/kg, at least 5 mg/kg, at least 10 mg/kg.

In a preferred embodiment, the CNNM4 inhibitor is administered once a day, twice a day, thrice a day, or more. In another preferred embodiment, the CNNM4 inhibitor is administered once a week, twice a week, 3 times a week, 4 times a week, 5 times a week, 6 times a week, 7 times a week, or more. In a more preferred embodiment, the CNNM4 inhibitor is administered twice a week.

Alternatively, the invention relates to a method for treating a liver disease, a kidney disease and/or a lung disease comprising administering a CNNM4 inhibitor or a pharmaceutical composition according to the invention to a subject in need thereof. All the terms and embodiments previously described are equally applicable to this aspect of the invention.

Alternatively, the invention relates to a CNNM4 inhibitor or a pharmaceutical composition according to the invention for the preparation of a medicament for treating a liver disease, a kidney disease and/or a lung disease. All the terms and embodiments previously described are equally applicable to this aspect of the invention.

A Method for Diagnosing Liver Disease, Kidney Disease or Lung Disease

In another aspect, the invention relates to an in vitro method for diagnosing liver disease, kidney disease and/or lung disease in a subject which comprises:
  (a) determining the expression level of CNNM4 in a sample from said subject, and
  (b) comparing said level with a reference value,
  wherein an increased expression level of CNNM4 in said sample with respect to the reference value is indicative that the patient suffers from a liver disease, a kidney disease or a lung disease.

The terms "liver disease", "kidney disease", "lung disease", "subject", "CNNM4 gene" and "reference value" have been previously defined in connection with other aspects of the invention. All the particular and preferred embodiments of the other aspects of the invention regarding these terms fully apply to this aspect.

The term "diagnosis" as used herein, refers both to the process of attempting to determine and/or identify a possible disease in a subject, i.e. the diagnostic procedure, and to the opinion reached by this process, i.e. the diagnostic opinion. As such, it can also be regarded as an attempt at classification of an individual's condition into separate and distinct categories that allow medical decisions about treatment and prognosis to be made. As the person skilled in the art will understand, such a diagnosis may not be correct for 100% of the subject to diagnose, although preferred it is. The term, however, requires that a statistically significant part of the subjects can be identified as suffering from a disease, particularly a liver disease, a kidney disease or a lung disease in the context of the invention, or having a predisposition thereto. The skilled in the art may determine whether a party is statistically significant using different statistical evaluation tools well known, for example, by determination of confidence intervals, the p-value determination, Student's-test, the Mann-Whitney, etc. (see Dowdy and Wearden, 1983). Preferred confidence intervals are at least, 50%, at least 60%, at least 70%>, at least 80%>, at least 90%) or at least 95%. The p-values are preferably, 0.05, 0.025, 0.001 or lower. The term "diagnosing" as disclosed herein means the process of determining which disease or condition explains a person's symptoms and signs.

In a particular embodiment, the method for diagnosing liver, kidney or lung disease of the invention comprises determining the expression level of CNNM4. Methods to determine expression level of CNNM4 are as disclosed elsewhere herein. In a preferred embodiment the method for diagnosing the liver, kidney or lung disease of the invention comprises determining the expression level of CNNM4 protein. In a more preferred embodiment the method for diagnosing the liver, kidney or lung disease of the invention comprises determining the expression level of CNNM4 protein by immunohistochemistry.

In an embodiment, when the expression level of CNNM4 is increased with respect to a reference value, the patient suffers from a liver disease, a kidney disease and/or a lung disease. Methods to determine the expression level of CNNM4 have been disclosed previously. In an embodiment, when the expression level of CNNM4 is increased with respect to the reference value by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, or more, the patient is diagnosed as suffering from a liver disease, a kidney disease and/or a lung disease.

As used herein, "sample" or "biological sample" refers to biological material isolated from a subject. The sample contains any material suitable for detecting the level of expression of a gene and may be a material comprising genetic material of the subject.

The biological sample may comprise cellular and/or non-cellular material of the subject, preferably cellular material. In a particular embodiment, the sample comprises genetic material, for example, DNA, genomic DNA (gDNA), complementary DNA (cDNA), RNA, mRNA, etc., of the subject under study. In a particular embodiment, the genetic material is RNA. The sample can be isolated from any biological tissue or fluid, such as, for example, blood, saliva, plasma, serum, urine, cerebrospinal fluid (CSF), feces, nasal, buccal or bucco-pharyngeal swabs, a specimen, a specimen obtained from a biopsy, and a sample of tissue embedded in paraffin, liver, lung or kidney tissue. The procedures for isolating samples are well known to those skilled in the art. The biological sample may contain any biological material suitable for detecting the expression level of CNNM4 and may comprise cellular and/or non-cellular material from the subject. Preferably, the samples used for the determination of the expression level of CNNM4 are samples which can be obtained using minimally invasive procedures. In a preferred embodiment, the sample is a liver, kidney and/or lung sample or biopsies.

Before analysing the sample, it will often be desirable to perform one or more operations of preparing said sample to separate the molecule to be determined from other molecules that are in the sample. In a particular embodiment, the molecules are nucleic acids, DNA and/or RNA. These sample preparation operations include manipulations such as: concentration, suspension, extraction of intracellular material (e.g., nucleic acids from tissue samples/whole cell and the like), nucleic acid amplification, fragmentation, transcription, labelling and/or extension reactions. These methods are well known to a person skilled in the art. Commercial kits for mRNA purification are also available, including, without limitation, miRNeasy Mini Kit from Qiagen, miRNA Life Technologies isolation kits, mirPremier the microRNA isolation kit from Sigma-Aldrich and High Pure miRNA Isolation Kit from Roche. In a particular embodiment the integrity of the RNA was analyzed using RNA 6000 Nano Chips in the Agilent 2100 bionalizer (Agilent Technologies, Palo Alto, CA, USA).

In an embodiment, when a patient is diagnosed as suffering from a liver disease, a kidney disease and/or a lung disease, a therapeutically effective amount of a CNNM4 inhibitor is administered to said patient.

As it is used herein, the term "therapeutic effective amount" is understood as any amount of the inhibitor according to the invention able to inhibit the expression of the CNNM4. In a preferred embodiment, if CNNM4 expression is found to be increased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100% with respect to a reference value, a therapeutic effective amount of a CNNM4 inhibitor is administered to the patient.

In a preferred embodiment the inhibitor is selected from the group consisting of a neutralising antibody or functional fragment thereof, an antagonist, a soluble binding protein, a soluble receptor variant, a non-functional derivative, an antisense polynucleotide, a RNA interference oligonucleotide, a phosphorodiamidate morpholino oligomer (PMO), miRNA, siRNA, shRNA, sgRNA antisense RNA, a dicer-substrate 27-mer duplex, an aptamer, a DNAzyme, a ribozyme, a triplex forming oligonucleotide (TFO), a small molecule and combinations thereof. In a more preferred embodiment the CNNM4 inhibitor is a siRNA. In an even more preferred embodiment, the siRNA comprises at least one of the nucleic acid sequences SEQ ID NO: 13, SEQ ID NO: 14, SEQ ID NO: 50 or SEQ ID NO: 51 or any of the sequences with SEQ ID NOs shown in Table 1. In a still more preferred embodiment the siRNA comprises the nucleic acid sequences set forth herein as SEQ ID NO: 7 and SEQ ID NO: 8.

In a preferred embodiment the liver disease is selected from liver fibrosis, veno-occlusive liver disease, drug-induced liver injury (DILI), steatosis, non-alcoholic steatohepatitis (NASH), cirrhosis, hepatocellular carcinoma (HCC), Budd-Chiari syndrome and hepatitis, or any combination thereof. In another preferred embodiment the kidney disease is selected from acute kidney injury (AKI), chronic kidney disease, nephritis, nephrosis and renal fibrosis, or any combination thereof. In another preferred embodiment the lung disease is pulmonary fibrosis.

All the terms and embodiments previously described are equally applicable to this aspect of the invention.

Use of Reagents for In Vitro Diagnosing a Disease

In a further aspect, the invention relates to the use of reagents specific for determining the expression level of CNNM4, for in vitro diagnosing a liver disease, a kidney disease or a lung disease in a subject.

The reagents specific for determining the expression level of CNNM4 may be presented in a kit format. In the context of the present invention, "kit" or "assay device" is understood as a product or device containing the different reagents necessary for carrying out the method of determining the expression level of CNNM4, packed so as to allow their transport and storage. Materials suitable for packing the components of the kit include crystal, plastic (polyethylene, polypropylene, polycarbonate and the like), bottles, vials, paper, envelopes and the like. Additionally, the kits can contain instructions for the simultaneous, sequential or separate use of the different components which are in the kit. Said instructions can be in the form of printed material or in the form of an electronic support capable of storing instructions such that they can be read by a subject, such as electronic storage media (magnetic disks, tapes and the like), optical media (CD-ROM, DVD) and the like. Additionally or alternatively, the media can contain Internet addresses that provide said instructions.

The expression "reagent specific for determining the expression level of CNNM4" means a compound or set of compounds that allows determining the expression level of a gene, both by means of the determination of the level of mRNA or by means of the determination of the level of protein. Thus, reagents of the first type include probes capable of specifically hybridizing with the mRNAs encoded by said genes. Reagents of the second type include compounds that bind specifically with the proteins encoded by the marker genes and preferably include antibodies, although they can be specific aptamers.

Accordingly, in a particular embodiment the reagents specific for determining the expression level of CNNM4 are selected from the group consisting of a set of probes which specifically hybridize to the mRNA of CNNM4 and a set of primer pairs which are capable of specifically amplifying the mRNAs of CNNM4, or wherein the reagent specific for determining the expression level of CNNM4 is an antibody which specifically binds to the CNNM4 polypeptide.

In a preferred embodiment, the reagents adequate for the determination of the expression levels of CNNM4 comprise at least 10%, at least 20%, at least 30%, at least 40%, at least 50%, at least 60%, at least 70%, at least 80%, at least 90% or at least 100% of the total amount of reagents adequate for the determination of the expression levels of genes forming the kit.

In a preferred embodiment, the first component of the kit of the invention comprises probes which can specifically hybridize to the gene mentioned above.

The term "specifically hybridizing", as used herein, refers to conditions which allow hybridizing of two polynucleotides under high stringent conditions or moderately stringent conditions.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and the hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide, followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mMNaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

In the event that the expression levels of CNNM4 is determined by measuring the levels of the polypeptide encoded by said gene, the kit according to the present use comprises reagents which are capable of specifically binding to said polypeptide. For this purpose, the arrays of antibodies such as those described by De Wildt et al. (2000) Nat. Biotechnol. 18:989-994; Lueking et al. (1999) Anal. Biochem. 270:103-111; Ge et al. (2000) Nucleic Acids Res. 28, e3, I-VII; MacBeath and Schreiber (2000) Science 289:1760-1763; WO 01/40803 and WO 99/51773A1 may be useful. The antibodies of the array include any immunological agent capable of binding to a ligand with high affinity, including IgG, IgM, IgA, IgD and IgE, as well as molecules similar to antibodies which have an antigen binding site, such as Fab', Fab, F(ab')2, single domain antibodies or DABS, Fv, scFv and the like. The techniques for preparing said antibodies are very well known for the person skilled in the art and include the methods described by Ausubel et al. (Current Protocols in Molecular Biology, eds. Ausubel et al, John Wiley & Sons (1992)).

The antibodies of the array can be applied at high speed, for example, using commercially available robotic systems (for example, those produced by Genetic Microsystems or Biorobotics). The substrate of the array can be nitrocellulose, plastic, crystal or can be of a porous material as for example, acrylamide, agarose or another polymer. In another embodiment, it is possible to use cells producing the specific antibodies for detecting the proteins of the invention by means of their culture in array filters. After the induction of the expression of the antibodies, the latter are immobilized in the filter in the position of the array where the producing cell was located. An array of antibodies can be put into contact with a labeled target and the binding level of the target to the immobilized antibodies can be determined. If the target is not labeled, a sandwich type assay can be used in which a second labeled antibody specific for the polypeptide which binds to the polypeptide which is immobilized in the support is used. The quantification of the amount of polypeptide present in the sample in each point of the array can be stored in a database as an expression profile. The array of antibodies can be produced in duplicate and can be used to compare the binding profiles of two different samples.

In an embodiment, the invention relates to the use of a kit or assay device comprising reagents adequate for the determination of the average expression level of the polypeptide encoded by the Cnnm4 genes wherein the reagents are an antibody or a set of antibodies which specifically bind to the polypeptide encoded by said gene and wherein said reagents comprise at least 10% of the reagents present in the kit.

In a particular aspect, the invention relates to the use of a kit of the invention for determination of the prognosis of a patient suffering from liver, kidney or lung disease. In a preferred embodiment the liver disease is selected from liver fibrosis, veno-occlusive liver disease, drug-induced liver injury (DILI), steatosis, non-alcoholic steatohepatitis (NASH), cirrhosis, hepatocellular carcinoma (HCC), Budd-Chiari syndrome and hepatitis, or any combination thereof. In another preferred embodiment the kidney disease is selected from acute kidney injury (AKI), chronic kidney disease, nephritis, nephrosis and renal fibrosis, or any combination thereof. In another preferred embodiment the lung disease is pulmonary fibrosis.

All the terms and embodiments previously described are equally applicable to this aspect of the invention.

Method of Reducing an Induced Disease or Condition

In a final aspect, the invention relates to an in vitro method of reducing an induced disease or condition in a cell, the method comprising contacting the cell with a specific CNNM4 inhibitor in an amount effective to decrease a CNNM4 activity, level or function in the cell.

The term "method of reducing an induced disease or condition in a cell" as used herein refers to a method for observing an increase or a decrease in the biomarker levels characteristic of a disease induced in a cellular model of said disease. In a particular embodiment, the induced disease or condition in a cell is an induced CNNM4-mediated disease of condition, wherein the disease concurs with increased CNNM4 expression with respect to a reference value. In an embodiment, the induced CNNM4-mediated disease of condition concurs with increased CNNM4 expression with respect to a reference value is characterised by an the expression level of CNNM4 that is increased with respect to the reference value by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, or more. In an embodiment, the reference value corresponds to the CNNM4 expression level in the same cellular system wherein the CNNM4-mediated disease of condition has not been induced. The same cellular system wherein the CNNM4-mediated disease of condition has not been induced may be used as a control.

In an embodiment, induced disease or condition in a cell is a disease model for the study of DILI, steatosis, NASH, cirrhosis, HCC, liver fibrosis, kidney fibrosis or lung fibrosis. In an embodiment, the induced disease or condition in a cell refers to a model cell system in culture. In an embodiment, the cell culture is a primary cell culture. In an embodiment, the induced disease or condition is induced in an animal model prior to culturing the cell. In a specific example, the induced disease or condition in a cell is NASH induced in primary hepatocytes.

In a particular embodiment, the animal model is a NAFLD animal model, wherein the NAFLD is induced by subjecting the animal (i.e. C57BL/6J wild type mice) to a methionine (0.1%) and choline (0%) deficient diet for 4 weeks, and subsequently harvesting the liver and culturing the relevant cells.

In a particular embodiment, the animal model is a cirrhosis animal model, wherein the cirrhosis is induced by subjecting the animal (i.e. C57BL/6J wild type mice) to bile duct ligation, sacrificing the animal after 1 to 21 days and harvesting the liver and culturing the relevant cells.

In a particular embodiment, the animal model is a hepatocellular carcinoma (HCC) animal model, wherein the HCC animal model, adult GNMT−/− mice spontaneously develop HCC. Animals are kept for 7 to 9 months, sacrificed, the liver is harvested and the relevant cells are cultured.

In a particular embodiment, the animal model is a drug induced liver injury (DILI) animal model, wherein the DILI is induced by subjecting the animal (i.e. adult C57BL/6J wild type mice) to a treatment with acetaminophen (APAP), 500 mg/kg to induce acute liver injury. After 48 hours animals are sacrificed, liver is harvested and the relevant cells are cultured.

As used herein, the term "biomarker" refers to the relevant read-out that is required to monitor progression in a specific disease model. In a particular embodiment the biomarker is the expression levels of CNNM4. In a particular embodiment the biomarker is the relative lipid accumulation. In a particular embodiment, the biomarker is the relative mitochondrial ROS (reactive oxygen species). In a particular embodiment, the biomarker is the percentage value of TUNEL positive cells. In a particular embodiment, the biomarker is the level of intracellular magnesium accumulation.

In another embodiment, the invention relates to a method for identifying a compound potentially useful for reducing an induced CNNM4-mediated disease or condition in a cell, the method comprising contacting the cell with a candidate compound in an amount effective to decrease a CNNM4 activity, level or function in the cell, or in an amount effective to reduce the relative lipid accumulation or to reduce the relative mitochondrial ROS with respect to a reference value, wherein a candidate compound that inhibits CNNM4 activity, reduces the relative lipid accumulation with respect to a reference value or reduces the relative mitochondrial ROS with respect to a reference value in an induced CNNM4-mediated disease or condition in a cell is identified as a compound potentially useful for treating and/or preventing a CNNM4-mediated liver, kidney and/or lung disease. In an embodiment, the reference value corresponds to the lipid accumulation level or to the mitochondrial ROS level in the same cellular system wherein the CNNM4-mediated disease of condition has been induced, but which has not been exposed to the compound. The same cellular system wherein the CNNM4-mediated disease of condition has not been induced may be used as a control.

The lipid accumulation in the cellular model system or the mitochondrial ROS level in the cellular system is considered to be reduced when its levels decrease with respect to the reference value by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95% or by at least 99%.

In yet another embodiment, the invention relates to a method for identifying a compound potentially useful for treating and/or preventing a CNNM4-mediated liver kidney and/or lung disease, the method comprising:
  (a) contacting the candidate compound with a cellular model of the disease; and
  (b) assaying a marker in the presence of said candidate compound, wherein the marker is selected from the group consisting of the activity of CNNM4 in the presence of a compound, the relative lipid accumulation with respect to a reference value, or the relative mitochondrial ROS with respect to a reference value, wherein a compound that inhibits CNNM4 activity, reduces the relative lipid accumulation with respect to a reference value or reduces the relative mitochondrial ROS with respect to a reference value is a compound potentially useful for treating and/or preventing a liver disease, a kidney disease and a lung disease.

In a particular embodiment, the candidate compound is selected from the group consisting of a neutralising antibody or functional fragment thereof, an antagonist, a soluble binding protein, a soluble receptor variant, a non-functional derivative, an antisense polynucleotide, a RNA interference oligonucleotide, a phosphorodiamidate morpholino oligomer (PMO), miRNA, siRNA, shRNA, sgRNA, antisense RNA, a dicer-substrate 27-mer duplex, an aptamer, a DNAzyme, a ribozyme, a triplex forming oligonucleotide (TFO), a small molecule and combinations thereof.

All the terms and embodiments previously described are equally applicable to this aspect of the invention.

The invention further discloses the following aspects:
1. A CNNM4 inhibitor for use in medicine.
2. A CNNM4 inhibitor for use in the treatment of an acute or a chronic disease in a subject, wherein the disease is selected from the group consisting of a liver disease, a kidney disease and a lung disease.
3. The CNNM4 inhibitor for use according to aspect 2, wherein said liver disease is selected from liver fibrosis, veno-occlusive liver disease, drug-induced liver injury (DIL), steatosis, non-alcoholic steatohepatitis (NASH), cirrhosis, hepatocellular carcinoma (HCC) and Budd-Chiari syndrome, hepatitis;
   wherein said kidney disease is selected from acute kidney injury (AKI), chronic kidney disease, nephritis, nephrosis and renal fibrosis;
   and wherein said lung disease is pulmonary fibrosis.
4. The CNNM4 inhibitor for use according to any one of aspects 1 to 3, wherein said inhibitor is selected from the group consisting of a neutralising antibody or functional fragment thereof, an antagonist, a soluble binding protein, a soluble receptor variant, a non-functional derivative, an antisense polynucleotide, a RNA interference oligonucleotide, a phosphorodiamidate morpholino oligomer (PMO), miRNA, siRNA, shRNA, sgRNA, antisense RNA, a dicer-substrate 27-mer duplex, an aptamer, a DNAzyme, a ribozyme, a triplex forming oligonucleotide (TFO), a small molecule and combinations thereof.
5. The CNNM4 inhibitor for use according to aspect 4, wherein the small molecule is 7-amino-2-phenyl-5H-thieno[3,2-c]pyridin-4-one or 2-[5-(4-Oxo-2-thioxo-thiazolidin-5-ylidenemethyl)-furan-2-yl]-benzoic acid.
6. An in vitro method for diagnosing liver disease, kidney disease or lung disease in a subject which comprises:
   (a) determining the expression level of CNNM4 in a sample from said subject, and
   (b) comparing said level with a reference value,
   wherein an increased expression level of CNNM4 in said sample with respect to the reference value is indicative that the patient suffers from a liver disease, a kidney disease or a lung disease.
7. The method according to aspect 6, wherein the sample is a liver, kidney or lung biopsy.
8. The method according to any one of aspects 6 or 7, wherein said liver disease is selected from liver fibrosis, veno-occlusive liver disease, drug-induced liver injury (DILI), steatosis, non-alcoholic steatohepatitis (NASH), cirrhosis hepatocellular carcinoma (HCC) and Budd-Chiari syndrome, hepatitis;

wherein said kidney disease is selected from acute kidney injury (AKI), chronic kidney disease, nephritis, nephrosis and renal fibrosis;

and wherein said lung disease is pulmonary fibrosis.

9. Use of reagents specific for determining the expression level of CNNM4, for in vitro diagnosing a liver disease, a kidney disease or a lung disease in a subject.

10. The use according to aspect 9, wherein said liver disease is selected from liver fibrosis, veno-occlusive liver disease, drug-induced liver injury (DILI), steatosis, non-alcoholic steatohepatitis (NASH), cirrhosis hepatocellular carcinoma (HCC) and Budd-Chiari syndrome, hepatitis;

wherein said kidney disease is selected from acute kidney injury (AKI), chronic kidney disease, nephritis, nephrosis and renal fibrosis;

and wherein said lung disease is pulmonary fibrosis.

11. The use according to any one of aspects 9 or 10, wherein the reagents specific for determining the expression level of CNNM4 are selected from the group consisting of a set of probes which specifically hybridize to the mRNA of CNNM4 and a set of primer pairs which are capable of specifically amplifying the mRNAs of CNNM4, or wherein the reagent specific for determining the expression level of CNNM4 is an antibody which specifically binds to the CNNM4 polypeptide.

12. An in vitro method of reducing an induced disease or condition in a cell, the method comprising contacting the cell with a specific CNNM4 inhibitor in an amount effective to decrease a CNNM4 activity, level or function in the cell.

13. An in vitro method for identifying a compound potentially useful for reducing an induced CNNM4-mediated disease or condition in a cell, the method comprising contacting the cell with a candidate compound in an amount effective to decrease a CNNM4 activity, level or function in the cell, or in an amount effective to reduce the relative lipid accumulation or to reduce the relative mitochondrial ROS with respect to a reference value, wherein a candidate compound that inhibits CNNM4 activity, reduces the relative lipid accumulation with respect to a reference value or reduces the relative mitochondrial ROS with respect to a reference value in an induced CNNM4-mediated disease or condition in a cell is identified as a compound potentially useful for treating and/or preventing a CNNM4-mediated liver, kidney and/or lung disease.

14. The method according to any one of aspects 12 or 13, wherein said inhibitor or said compound is selected from the group consisting of a neutralising antibody or functional fragment thereof, an antagonist, a soluble binding protein, a soluble receptor variant, a non-functional derivative, an antisense polynucleotide, a RNA interference oligonucleotide, a phosphorodiamidate morpholino oligomer (PMO), miRNA, siRNA, shRNA, sgRNA, antisense RNA, a dicer-substrate 27-mer duplex, an aptamer, a DNAzyme, a ribozyme, a triplex forming oligonucleotide (TFO), a small molecule and combinations thereof.

The invention will also be described by way of the following examples which are to be considered as merely illustrative and not limitative of the scope of the invention.

EXAMPLES

Materials and Methods

Human Samples

All the studies were performed in agreement with the Declaration of Helsinki and according to local national laws. The Human Ethics Committee of each hospital approved the study procedures and written informed consent was obtained from all patients before inclusion in the study.

Magnesium was quantified from human serum samples from a cohort of 8 healthy samples, 31 obese-diagnosed patients and 43 from a cohort of clinical trials. Patients were evaluated for non-alcoholic fatty liver disease (NAFLD) by different markers once discarded alcoholic disease and viral hepatitis infection.

Human CNNM4 expression in non-alcoholic fatty liver disease NAFLD was determined in a cohort of 42 patients: 10 healthy patients, 20 patients diagnosed with steatosis and 12 diagnosed with NAFLD.

The CNNM4 levels in cirrhotic patients were determined in a cohort of 12 patients from which 5 were diagnosed as healthy and 7 as cirrhotic. 47 hepatocellular carcinoma (HCC) patients' CNNM4 levels were also determined: 6 patients were healthy and 41 patients were diagnosed HCC.

CNNM4 levels were determined in a cohort of 11 drug-induced liver injury (DILI) patients and compared to 3 healthy patients.

Finally, renal fibrosis 14 human samples were analysed to determine CNNM4 expression. 7 samples were healthy and another 7 have been diagnoses with renal fibrosis.

Animal Experiments

All the animal experiments were conducted in accordance with the Spanish Guide for Care and use of Laboratory animals, and with the International Care and Use Committee Standards. All procedures were approved by the CIC bioGUNE's Animal Care and Use Committee and the competent authority (Diputación de Bizkaia). Mice were housed in a temperature-controlled animal facility (AAALAC-accredited) within 12-hour light/dark cycles. G-They were fed a standard diet (Harlan Tekland) with water ad libitum.

NAFLD Animal Model: 0.1% Methionine and Choline-Deficient Diet (0.1% MCDD) for CNNM4 Determination C57BL/6J wild-type mice were fed with a methionine (0.1%) and choline (0%) deficient diet for 4 weeks. At the end of the treatment animals were sacrificed and liver were split into several pieces for subsequent analysis including: RNA or protein extraction, formalin fixation for histology and immunohistochemistry or metabolic analysis. Blood for serum analysis was collected once a week during the treatment.

Pre-Clinical Study: NAFLD Animal Model with siRNA Therapy

C57BL/6J wild-type mice were fed with a methionine (0.1%) and choline (0%) deficient diet for 4 weeks. 2 weeks after the beginning of the diet mice were divided in two groups and subjected to an in vivo silencing CNNM4 or unrelated siRNA control, receiving either 200 μl of a 0.75 μg/μl solution of or CNNM4-specific in vivo siRNA (Custom Ambion, USA) or control siRNA (Sigma-Aldrich, USA) using Invivofectamine® 3.0 Reagent (Invitrogen, USA) following the manufacturer's instructions. Tail vein injection was performed twice a week until the fourth week. At the end of the treatment animals were sacrificed and liver were split into several pieces for subsequent analysis including: RNA or protein extraction, formalin fixation for histology and immunohistochemistry or metabolic analysis. Blood for serum analysis was collected once a week during the treatment.

Cirrhosis Animal Model: Bile Duct Ligation (BDL)

Adult C57BL/6J wilt-type mice were subjected to BDL as described previously (Fernández-Álvarez et al., 2015. *Lab Invest.* 95(2):223-36). Briefly, mice were anesthetized with 1.5% isofluorane in 02 and the abdomen was opened. The bile duct was separated from the portal vein and the hepatic artery, performing a suture around the bile duct and securing with a surgical know. Finally, the abdomen was closed and mice sacrificed at 24 h, 48 h, 72 h, 3 days and 21 days. Liver were split into several pieces for subsequent analysis including: RNA or protein extraction, formalin fixation for histology and immunohistochemistry or metabolic analysis. Blood for serum analysis was collected once a week during the treatment.

Hepatocellular Carcinoma Animal Model (HCC): GNMT-/- Mice

Adult GNMT$^{-/-}$ mice were grown from 7 to 9 months, when they are described to develop spontaneously HCC (Wagner et al., 2009. *Toxicol Appl Pharmacol.* 1; 237(2):246; author reply 247). At that time animals were sacrificed and liver were split into several pieces for subsequent analysis including: RNA or protein extraction, formalin fixation for histology and immunohistochemistry or metabolic analysis. Blood for serum analysis was collected once a week during the treatment.

Drug Induced Liver Injury (DILI): Acetaminophen (APAP) Overdose

Adult C57BL/6J wilt-type mice were treated with 500 mg/kg of acetaminophen (APAP) to induce acute liver injury. After 48 h of treatment, mice were sacrificed and liver were split into several pieces for subsequent analysis including: RNA or protein extraction, formalin fixation for histology and immunohistochemistry or metabolic analysis. Blood for serum analysis was collected once a week during the treatment.

Isolation of Primary Hepatocytes, Culture and Treatments

Primary hepatocytes from 3-month old wild type (C57BL/6J) mice were isolated by perfusion with collagenase Type I (Worthington, USA). Briefly, animals were anesthetized with isoflurane (1.5% isoflurane in $O_2$). Then, the abdomen was opened and a catheter was inserted into the inferior vena cava. Liver was perfused with buffer A (1×PBS, 5 mM EGTA, 37° C. and oxygenated) and the portal vein was cut. Next, liver was perfused with buffer B (1×PBS, 1 mM $CaCl_2$ 37° C. and oxygenated) to remove EGTA, and finally perfused with buffer C (1×PBS, 2 mM $CaCl_2$, 0.65 BSA, collagenase type I, 37° C. and oxygenated). After buffer C perfusion, liver was separated from the resto of the body and placed into a petri dish with MEM (Gibco, USA). Gall bladder was carefully removed and, then, liver was mechanically disaggregated with forceps. The digested liver diluted in MEM was filtered through a sterile gauze and filtered liver cells were collected and washed three times (1×4' at 400 RPM and 2×5' at 500 RPM) in 10% FBS (Gibco)/1% PSG (Gibco) supplemented MEM, conserving all supernadant Kupffer and Hepatic Stellate cells isolation. After the final wash, hepatocytes contained in the pellet were resuspended in 10% FBS 1% PSG MEM for subsequently culturing.

Primary hepatocytes were seeded over previously collagen-coated culture dishes at a density of 7600 cells/mm$^2$ in 10% FBS/1% PSG supplemented MEM and placed in an incubator at 37° C., 5% $CO_2$-95% air. After 6 hours of attachment, culture medium and unattached hepatocytes were removed with fresh 0% FBS/1% PSG MEM for the aimed treatment (Table 2).

TABLE 2

Reagents used for in vitro experiments.

| Reagent | Dose | Vehicle | Time | Function | % FBS | Supplier |
|---|---|---|---|---|---|---|
| Acetaminophen (APAP) | 10 mM | PBS 1x | 6 h | DILI in vitro model. | 0% FBS | Sigma Aldrich |
| Magnesium-deficient medium | 0 mM | | 24 h | Medium without magnesium. | 0% FBS | GE HealthCare |
| Magnesium-enriched medium | 5 mM | MEM/ MCD medium | 24 h | Enrich culture medium with magnesium. | 0% FBS | Sigma Aldrich |
| Methionine and Choline Deficient (MCD) medium | | | 24 h | Increase hepatocytes lipid content. | 0% FBS | Gibco |
| 7-amino-2-phenyl-5H-thieno[3,2-c]pyridin-4-one (thienopyridone) | 5 nM-10 mM | DMSO | 24 h | CNNM4 potential inhibitor. | 0% FBS | Enamine |

THLE2 Cells

THLE-2 cells were purchased from ATCC (ATCC® CRL-2706™). They were maintained on Bronchial Epithelial Growth Medium (BEGM™, Lonza) supplemented with BEGM Bullet Kit™ (Lonza) and 10% FBS. They were split with 0.05% trypsin-EDTA and collected in BEGM. After centrifugation at 123 g during 5 minutes, supernatant was discarded and pellet resuspended.

Plasmid Transfection

Plasmids were transfected into primary mouse hepatocytes for overexpression using jetPRIME® (Polyplus, USA) transfection reagent following manufacturer's protocol. In a 24-well plate, 0.5 µg of plasmid were added to the jeP-RIME® buffer and vortexed 10 s before adding 1 µl jetPRIME® reagent. The mix was vortexed 10 s, spinned down and incubated 10' at RT). Transfections were performed in cell suspension medium and transfection mix was replaced for fresh medium 6 h after transfection unless indicated.

Gene Silencing by siRNA Delivery

Cells were transfected with specific siRNAs at a final concentration of 100 nM using DharmaFECT 1 reagent (Dharmacon) following manufacturer's protocol. Dharma- FECT 1 and siRNA were diluted separately in 0% FBS/1% PSG MEM for 5' at RT. Dilutions were then mixed and incubated 20' at RT. siRNA transfection mixed were then added to cell suspension medium and replaced for fresh medium after 6 h. siRNA transfection volumes, indicated for 6-well plates) and sequences are summarized in Table 3.

TABLE 3 siRNAs transfected with DharmaFECT 1 indicated for 6-well seeded cells.

| siRNA | DharmaFECT 1 (volume in X ml medium) | siRNA (100 µM) (volume in X ml medium) | Sequence | Final volume Medium |
|---|---|---|---|---|
| Cnnm 1 Mus musculus | 8 µl in 0.2 ml | 1 µl in 0.2 ml | SEQ ID NO 1: Sense 5'-GAUCCUGAAUGCUGUA AUAUU -3' SEQ ID NO 2: Antisense 5'-UAUUACAGCAUUCAGG AUCCG -3' SEQ ID NO 3: Sense 5'-ACGUGAUCCAGGAGCU UAAUU -3' SEQ ID NO 4: Antisense 5'-UUAAGCUCCUGGAUCA CGUTG -3' | 2 ml |
| Cnnm2 mus musculus | 8 µl in 0.2 ml | 1 µl in 0.2 ml | SEQ ID NO 5: Sense 5'-CTCAATTTGCATGAAAT TTAA -3' SEQ ID NO 6: Antisense 5'-UUAAAUUUCAUGCAAA UUGAG -3' SEQ ID NO 7: Sense 5'-CGGAGAAAGAGAAGAA UUAUU -3' SEQ ID NO 8: Antisense 5'-UAAUUCUUCUCUUUCU CCGTG -3' | 2 ml |
| Cnnm3 mus musculus | 8 µl in 0.2 ml | 1 µl in 0.2 ml | SEQ ID NO 9: Sense 5'-GAUGAUGAAUAUAAAG UAAUU -3' SEQ ID NO 10: Antisense 5'-UUACUUUAUAUUCAUC AUCAG -3' SEQ ID NO 11: Sense 5'-GGGCAGAGUCGAGGUC GAAUU -3' SEQ ID NO 12: Antisense 5'-UUCGACCUCGACUCUG CCCTG -3' | 2 ml |
| Cnnm4 mus musculus | 8 µl in 0.2 ml | 1 µl in 0.2 ml | SEQ ID NO 13: Sense 5'-CACUAUUGUUCUCACC AAAUU-3' SEQ ID NO 14: Antisense 5'-UUUGGUGAGAACAAUA GUGTT- 3' | 2 ml |

TABLE 3-continued siRNAs transfected with DharmaFECT 1 indicated for 6-well seeded cells.

| siRNA | DharmaFECT 1 (volume in X ml medium) | siRNA (100 μM) (volume in X ml medium) | Sequence | Final volume Medium |
|---|---|---|---|---|
| CNNM4 homo sapiens | 8 μl in 0.2 ml | 1 μl in 0.2 ml | SEQ ID NO 50: Sense 5'-CCAUGUCGGAGAUAAU GGATT -3' SEQ ID NO 51: Antisense 5'-UCCAUUAUCUCCGACA UGGTG-3' | 2 ml |

Gene Silencing by shRNA Delivery

Cells were transfected with specific shRNAs by using Lipofectamine® 3000 (Thermofisher) and following the protocol according manufacturer instructions. 7.5 μl lipofectamine and 3shRNA were diluted separately in 0.2 ml culture medium and incubated during 5' at room temperature. After incubation they were mixed again and incubated for 30' at room temperature before delivering to the cells. shRNA transfection volumes are indicated for 6-well plates and sequence is SEQ ID NO 52:

(SEQ ID NO 52)
5'-UCUCUGCCUUCAAGGAUGCGGACAAUGAG-3'

RNA Isolation and cDNA Expression Determination

RNA Isolation

Total RNA from whole liver or cultured cells was isolated using TRIzol reagent (Invitrogen) according to manufacturer's instruction. In case of cell mRNA extraction, 5 μg of Glycogen (Ambion, USA) were used in the RNA precipitation step to facilitate the visibility of the RNA pellet. RNA concentration was determined spectrophometrically using the Nanodrop ND-100 spectrophotometer (ThermoFisher Scientific, USA).

Retrotranscription 1-2 μg of isolated RNA were treated with DNAse I (Invitrogren) and used to synthesize cDNA by M-MLV reverse transcriptase in the presence of random primers and RNAseOUT (all from Invitrogen). Resulting cDNA was diluted 1/10 (1/20 if 2 μg were used) in RNAse free water (Sigma-Aldrich).

Real Time Quantitative PCR (RT-qPCR)

qPCRs were performed using either the ViiA 7 or the QS6 Real time PCR System with SYBR Select Master Mix (Applied Biosystems, USA). 1.5 μl of cDNA were used and including the specific primers for a total reaction volume of 6.5 μl in a 384-well plate (Applied Biosystems). All reactions were performed in triplicate. PCR conditions for the primers were optimized and 40 cycles with a melting temperature of 60° C. and 30 s per step were used. Both Homo Sapiens and Mus musculus primers were designed using the Primer 3 software via the NCBI-Nucleotide webpage (ncbi.nlm.nih.gov/nucleotide) and synthesized by Sigma Aldrich. Primer sequences are detailed in Table 4 and in Table 5. After checking the specificity of the PCR products with the melting curve, data were normalized to the expression of a housekeeping gene (GAPDH, ARP).

TABLE 4

List of primers used to determine mRNA expression of Mus musculus genes.

| Gene symbol | Forward sequence | Reverse sequence |
|---|---|---|
| Arp | SEQ ID NO 15: CGACCTGGAAGTCCAACTAC | SEQ ID NO 16: ATCTGCTGCATCTGCTTG |
| Cnnm1 | SEQ ID NO 17: CAACGAGGGTGAAGGAGACC | SEQ ID NO 18: CGTCGAGGATCTCCGACTTG |
| Cnnm2 | SEQ ID NO 19: GCGAGGCTATCCTGGACTTC | SEQ ID NO 20: TGTTGGAACGTTCTCCCTCG |
| Cnnm3 | SEQ ID NO 21: CTATCGTTGAGCCCGAGGAC | SEQ ID NO 22: GGACAGCGTCCAGTTTGGTA |
| Cnnm4 | SEQ ID NO 23: AGGTGAACAATGAGGGCGA | SEQ ID NO 24: CCGGGTCCGATTATCAGTGTA |

TABLE 5

List of primers used to determine mRNA expression of Homo sapiens genes.

| Gene symbol | Forward sequence | Reverse sequence |
|---|---|---|
| Arp | SEQ ID NO 53: CGACCTGGAAGTCCAACTAC | SEQ ID NO 54: ATCTGCTGCATCTGCTTG |
| CNNM4 | SEQ ID NO 55: GAGCTGCAACAACTCGTGTG | SEQ ID NO 56: TCCACCTCGGTGAAGGAGAT |

Protein

Protein Extraction and Analysis

Extraction of total protein was performed as indicated. Cells were washed with cold PBS buffer and resuspended in 200 μl of RIPA lysis buffer (1.6 mM NaH2PO4, 8.4 mM Na2HPO4, 0.5% Azide, 0.1 M NaCl, 0.1% SDS, 0.1% Triton X-100, 5 mg/ml sodium deoxycholate). The lysis buffer was supplemented with protease and phosphatase inhibitor cocktails (Roche, Switzerland). They were centrifuged (13000 rpm, 20' at 4° C.) and the supernatand (protein extract) was quantified for total protein content by the Bradford protein assay (Bio-Rad) and determined using a Spectramax M3 spectrophotometer (Molecular Devices, USA).

In the case of frozen liver tissue, approximately 50 μg of tissue was homogenized by using a Precellys 24 tissue homogenizer (Precellys, France) in 500 μl of buffer. In all cases, the lysates were centrifuged (13000 rpm, 20 min, 4° C.) and the supernatant (protein extract) was quantified for total protein content by the Bradford protein assay or by BCA protein assay (Pierce, USA) depending on the type of lysis buffer used and determined using a Spectramax M3 spectrophotometer.

Western Blotting

Protein extracts were boiled at 95° C. for 5 min in SDS-PAGE sample buffer (250 mM Tris-HCl pH 6.8, 500 mM β-mercaptoethanol, 50% glycerol, 10% SDS and bromophenol blue). An appropriate amount of protein (between 5 and 50 pig), depending on protein abundance and antibody sensitivity, were separated by sodium dodecyl sulphate-polyacrylamide gel electrophoresis (SDS-PAGE) in 3% to 15% acrylamide gels (depending on the molecular weight of the protein of interest), using a Mini-PROTEAN Electrophoresis System (Bio-Rad). Gels were transferred onto nitrocellulose membranes by electroblotting using a Mini Trans-Blot cell (Bio-Rad). Membranes were blocked with 5% nonfat milk in TBS pH 8 containing 0.1% Tween-20 (Sigma Aldrich) (TBST-0.1%), for 1 hour at RT, washed three times during 10' with TBST-0.1% and incubated overnight at 4° C. with commercial primary antibodies. Primary antibodies and their optimal incubation conditions are detailed in Table 6. Membranes were then washed three times during 10' with TBST-0.1% and incubated for 1 hour at RT in blocking solution containing secondary antibody conjugated to horseradish-peroxidase (HRP, Table 6). Immunoreactive proteins were detected by using Western Lightning Enhanced Chemiluminescence reagent (ECL, PerkinElmer, USA) and exposed to Super Rx-N X-ray films (Fuji, Japan) in a Curix 60 Developer (AGFA, Belgium).

TABLE 6

List of antibodies used for Western Blot.

| Antibody | Id | Supplier | Dilution | Incubation solution |
|---|---|---|---|---|
| CNNM4 | 14066-1-AP | Proteintech | 1/1000 | 5% nonfat milk in TBST-0.1% |
| GAPDH | AB8245 | Abcam | 1/10000 | 5% nonfat milk in TBST-0.1% |
| HRP-conjugated secondary antibody to mouse | #7076 | Cell Signalling | 1/1000 | 5% nonfat milk in TBST-0.1% |
| HRP-conjugated secondary antibody to rabbit | #7074 | Cell Signalling | 1/1000 | 5% nonfat milk in TBST-0.1% |

Staining Assays

Sudan Red for Lipid Staining

O.C.T-included frozen liver samples were cut into 10 μm sections. Sections were washed in 60% isopropanol and then stained with fresh Sudan III (0.5% in isopropanol; Sigma Aldrich) solution for 30 min. Samples were then washed again in 60% isopropanol and then counterstained with hematoxylin and eosin. The sections were then washed with distilled water and mounted in DPX mounting medium. Images were taken with an upright light microscope (Zeiss).

ROS Determination by DHE

O.C.T-embebed 8 μm sections were incubated with MnTBAP 150 μM 1 h at RT. The samples were then incubated with dihydroethidium (DHE) 5 μM for 30 min at 37° C. and sections were mounted with Fluoromount-G (Southern Biotech, USA) containing 0.7 mg/l of DAPI to counterstain nuclei. Images were taken using an Axioimager D1 (Zeiss).

Immunohistochemistry for CNNM4 Determination

Paraffin-embebed sections (5 μm thick) were unmasked according to the primary antibody to be used and subjected to peroxide blocking (3% $H_2O_2$ in PBS, 10', RT). For stainings with mouse-hosted antibodies in mouse tissues, samples were blocked with goat anti-mouse Fab fragment (Jackson Immunoresearch, USA) (1:10, 1 h, RT) and the blocked with 5% goat serum (30', RT). Then, section were incubated in a humid chamber with the CNNM4 primary antibody (Ab191207, Abcam) in DAKO antibody diluent (DAKO) at 1:100 followed by Envision anti rabbit (DAKO) HRP-conjugated secondary antibody incubation (30', RT). Colorimetric detection was confirmed with Vector VIP chromogen (Vector) and sections were counterstained with hematoxylin. Samples were mounted using DPX mounting medium. Images were taken with an upright light microscope (Zeiss).

Immunofluorescence for αSMA Determination

For α-SMA staining, O.C.T-embebed 10 μm sections were incubated with a 1/200 dilution in 2% BSA in 0.01% PBS-azide of the primary antibody conjugated to Cy3 (C6198, Sigma Aldrich) and mounted with Fluoromount-G (Southern Biotech) containing 0.7 mg/l of DAPI to counterstain nuclei. Images were taken using an Axioimager D1 (Zeiss).

BODIPY for Lipid Quantification in Primary Hepatocytes

Primary hepatocytes cultured in high lipid content medium (OA) or methionine/choline deficient medium (MDMC) were fixed in 4% paraformaldehyde (10', RT) in PBS and incubated with BODIPY 493/503 (Molecular Probes, Invitrogen) at 1 mg/ml (1 h, RT). BODIPY immunocytofluorescence images were taken using an Axioimager D1 (Zeiss) microscope. Quantification of lipid bodies was performed using Frida Software and represented as mean area per total number of cells.

Data Analysis

The average sum of intensities or stained area percentage of each sample were A calculated using the FRIDA software (bui3.win.ad.jhu.edu/frida/, John Hopkins University).

Liver Lipid Quantification 30 mg of frozen liver were homogenized with 10 volumes of ice-cold PBS in a potter homogenizer. Fatty acids were measured in the homogenates using the Wako Chemicals kit (Richmond, VA) and lipids were quantified as described (Folch et al., 1957. *J Biol Chem.* 226(1):497-509). Briefly, lipids were extracted from 1.5 mg of protein from liver homogenates. Phosphatidilcholine (PC), phosphatidylethanolamine (PE), fatty acids (FAs) and cholesterol (Ch) were separated by thin layer chromatography (TLC) and quantified as described (Ruiz and Ochoa, 1997). Triglycerides (TGs) were measured in the lipid extract with the A. Menarini Diagnostics (Italy) kit.

Magnesium Determination Assays

Intracellular Magnesium Levels

Primary hepatocytes grown in glass coverslips were loaded with 2 μM Mag-S-Tz or 1 μM Mag-S-Tz-AM diluted REF (Gruskos et al., 2016. *J. Am. Chem. Soc.* 138 (44), pp 14639-14649) in 0% FBS/1% PSG medium and incubated at 37° C. and 5% $CO_2$ during 30' or 1 h respectively. After removing the dye-containing medium, a 30' incubation in 0% FBS/1% PSG was performed. Coverslips were then washed in a 20 mM Tris-HCl, 2.4 mM $CaCl_2$, 10 mM glucose, pH 7.4 buffer and mounted on a thermostatitez perfusion chamber on a Eclipse TE 300-based microspectrofluorometer (Nikon, USA) and visualized with a 40× oil-immersion fluorescence. Intracellular $Mg^{2+}$ levels were determines using the method described by Grynkiewicz (Grynkiewiz et al., 1985. *J Biol Chem.* 260(6):3440-50). The 340/380 nm excited light ratio was determined with a Delta system (Photon Technologies International, Princeton) and converted into $Mg^{2+}$ concentration from the standard equation:

$$[Mg^{2+}]i = \frac{(R - R_{min})}{(R_{max} - R)} \times K_d \times Q$$

Where $K_d$ is the $Mg^{2+}$ dissociation constant of Mag-S-Tz (3.2 mM) and Mag-S-Tz-AM (8.9 mM) and Q is the ratio of the minimum/maximum fluorescence intensity at 380 nm.

Extracellular Magnesium Levels

Extracellular magnesium was quantified using the QuantiCrom™ Magnesium Assay Kit (BioAssay Systems, USA). Briefly, 5 µl of serum or culture media were mixed with 200 µl of a 1:1 mix of Reagent A and Reagent B. After 2' incubation at RT, OD was determined at 500 nm length using a Spectramax M3 spectrophotometer (Molecular Devices, USA). Then, 10 µl of EDTA were added and $OD_{500}$ was determined again. Magnesium concentrations were finally calculated by comparing to the $OD_{500}$ from a standard concentration (2 mg/ml).

In Vitro Assays

Mitochondrial ROS Determination

Mitochondrial ROS was measured using MitoSOX™ Red reagent (Life Technologies), following manufacturer's instructions. Briefly, primary hepatocytes and hepatoma cells were incubated with MitoSOX reagent (2.5 µM, 10', 37° C. in a CO2 incubator) in normal culture medium. Then, cells were washed twice with PBS and the fluorescence was measured at an excitation of 510 nm and emission of 595 nm using a spectrophotometer. Final values were normalized to total protein concentration.

Cell Death Determination by TUNEL

Cell Death was analysed by using the In situ Cell Death detection Kit (Roche) following the manufacturer's instructions as above indicated. Cells were subjected peroxide block (3% $H_2O_2$ in methanol) for 3 minutes before incubation with TUNEL diluent buffer containing FITC-conjugated primary antibody (dilution 1/50) for 1 hour at 37° C. Sections were mounted in Dako fluorescence mounting medium (Dako). Images were taken using an Axioimager D1 (Zeiss) microscope and cell viability was calculated by determining the % of TUNEL positive cells.

Results

CNNM4 Overexpression in Liver Pathologies

Figure 2:
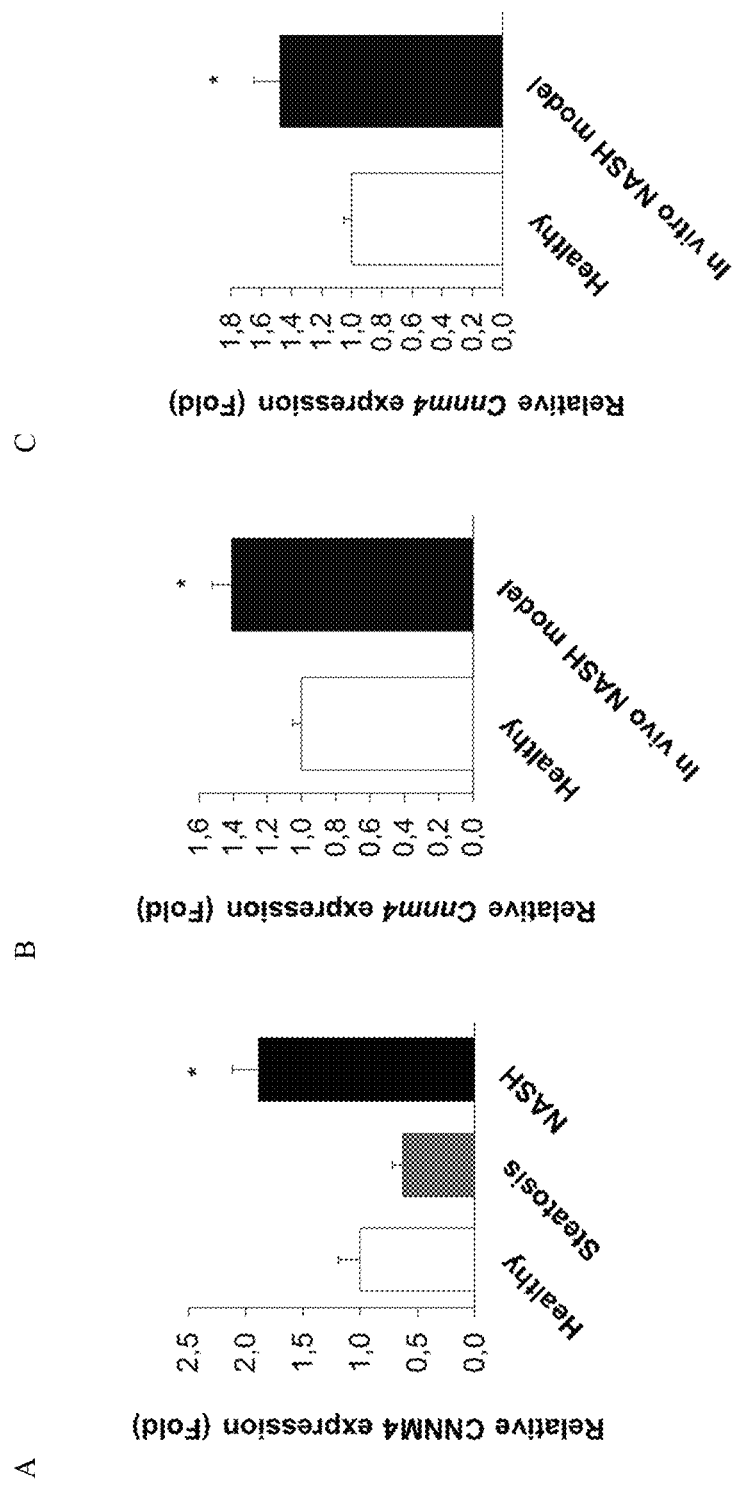
FIG. 2. A) CNNM4 expression, determined by qPCR of CNNM4 mRNA levels in human liver samples from healthy subjects compared with samples from steatotic and NASH patients. B) CNNM4 expression, determined by qPCR of CNNM4 mRNA levels in an in vivo mouse model. C) CNNM4 expression, determined by qPCR of CNNM4 mRNA levels in an in vitro mouse cell model. $*p<0.05$ vs Healthy.

Chronic liver disease includes a group of different pathologies. A method to detect CNNM4 expression by immunohistochemistry (IHC) in human liver biopsies and livers from mouse animal models has been developed. Herein CNNM4 expression has been characterized in DILI and all the stages from chronic liver disease, both in human biopsies and animal models, observing an overexpression of the protein in all the pathologies (FIG. 1). These results were confirmed by a method to detect CNNM4 expression by qPCR of CNNM4 mRNA levels in human liver samples from healthy subjects compared with samples from steatotic and NASH patients (FIG. 2A). CNNM4 expression could also be determined by qPCR of CNNM4 mRNA levels in an in vivo NASH mouse model (FIG. 2B), as well as in an in vitro NASH mouse cell model (FIG. 2C).

CNNM4 a New Target for Treating Liver Disease

Figure 3:
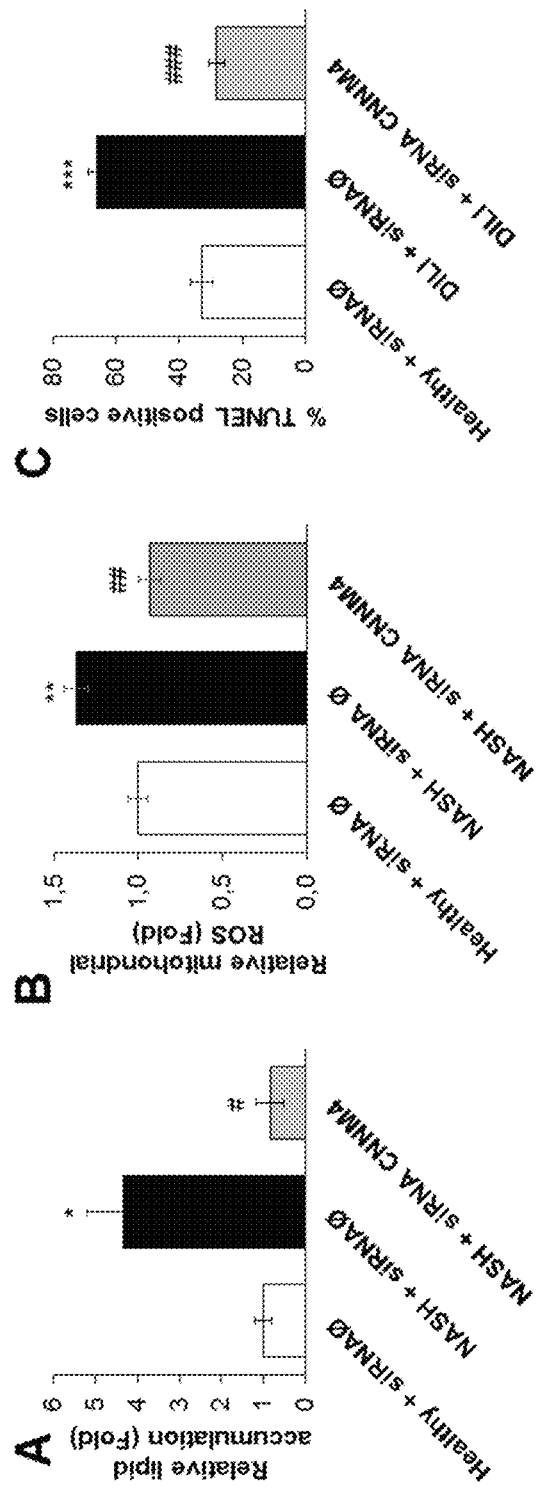
FIG. 3. A) Lipid content in NASH-induced primary hepatocytes return into healthy levels when treated with siRNA CNNM4. B) Inflammation induced by ROS also gets restored in treated mice and C) DILI-induced cell death gets ameliorated when treating hepatocytes with siRNA therapy. $*p<0.05$ vs Healthy $p<0.01$ vs Healthy; $*p<0.001$ vs Healthy; $\#p<0.05$ vs NASH; $\#\#p<0.01$ vs NASH; $\#\#\#p<0.001$ vs DILI.
Figure 4:
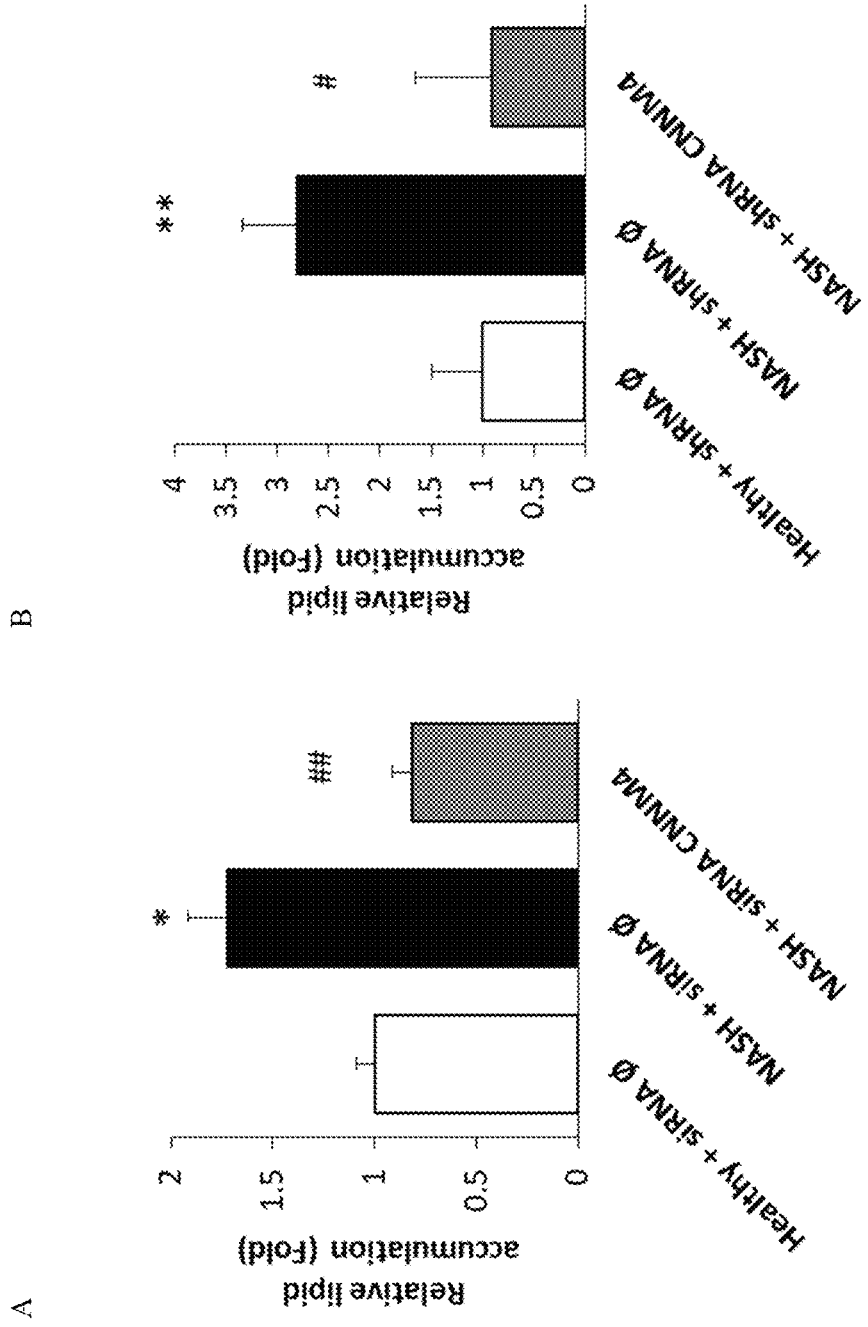
FIG. 4. A) Lipid content in NASH-induced human cells return to healthy levels when treated with siRNA CNNM4. B) Lipid content in NASH-induced human cells returns to healthy levels when treated with shRNA CNNM4. $*p<0.05$ vs Healthy $**p<0.01$ vs Healthy; $\#p<0.05$ vs NASH control; $\#\#p<0.01$ vs NASH control.

The overexpression observed in CNNM4 determination by IHC showed previously suggests CNNM4 as a potential target for treating liver disease, both for DILI and chronic disease. An in vitro study was performed inducing NASH in primary hepatocytes and treating them with a siRNA CNNM4 therapy. In case of NASH model-primary hepatocytes the lipid content and inflammation by reactive oxygen species (ROS) were measured, observing that both get restored in NASH hepatocytes treated with the siRNA therapy (FIGS. 3A and 3B). It was also performed another in vitro study emulating DILI by an acetaminophen overdose, observing an expected cell death in the DILI model-hepatocytes and a restoration when treating the cells with a targeted siRNA therapy (FIG. 3C). Further, an in vitro study was performed inducing NASH in human cells and treating them with a siRNA CNNM4 therapy or with a shRNA CNNM4 therapy, and the lipid content was measured, observing that the relative lipid accumulation gets restored both in NASH-induced human cells (THLE2 cells) treated with the siRNA therapy (FIG. 4A) and in NASH-induced human cells treated with the shRNA therapy (FIG. 4B).

Specificity and Need of Targeting CNNM4

Figure 5:
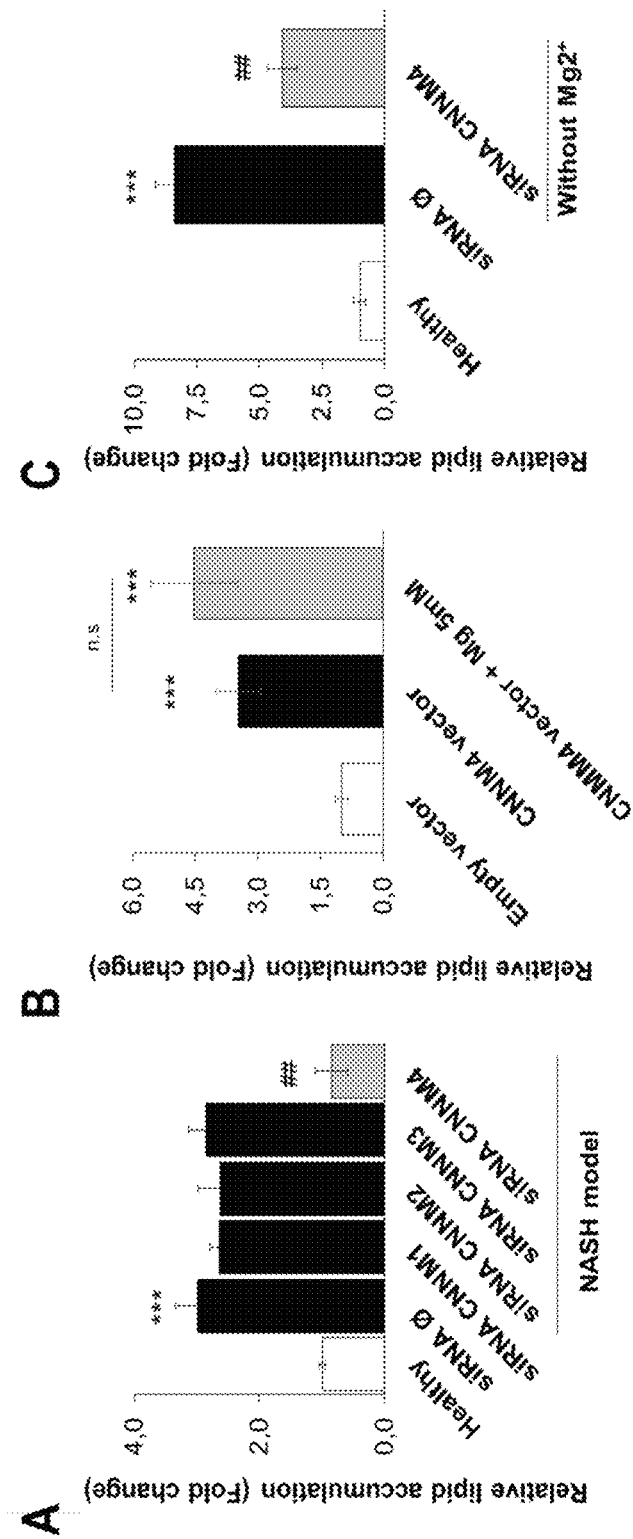
FIG. 5. A) Lipid content in NASH-induced primary hepatocytes does not return into healthy levels if they are treated with siRNA CNNM1, siRNA CNNM2 nor siRNA CNNM3. B) In case of a CNNM4 overexpression, magnesium supplementation does not reduced lipid content in primary hepatocytes. C) The siRNA CNNM4 treatment in primary hepatocytes reduces lipid accumulation caused by magnesium deficiency. $***p<0.001$ vs Healthy; $\#\#p<0.01$ vs NASH model/Without Mg2++ siRNA Ø.

Having observed the protective effect of siRNA CNNM4-therapies from NASH and DILI, the effect of targeted silencing the other proteins of CNNM family (CNNM1, CNNM2 and CNNM3) was determined. NASH was induced in primary hepatocytes and they were treated with siRNA CNNM1, CNNM2 and CNNM3. Differently than in siRNA CNNM4 therapy, silencing the other proteins of CNNM family had no effect, indicating the specificity of the treatment based only in CNNM4 and not in proteins of CNNM family (FIG. 5A). Furthermore, experiments have been realized in order to prove the need of a CNNM4-based treatment. In the first case lipid accumulation was induced in primary hepatocytes by a CNNM4 overexpression, similarly as observed in NASH patients and animal models, and then they were supplemented with magnesium. Magnesium supplementation has no effect in decreasing lipid accumulation similarly as siRNA CNNM4 treatment has (FIG. 5B). Secondly, lipid accumulation was induced by magnesium deprivation in primary hepatocytes, a physiological condition similar as the CNNM4 overexpression. In this case, siRNA CNNM4 therapy reduced lipid accumulation (FIG. 5C). Taking into account the last two results, magnesium supplementation is not enough for treating NASH so there is a need of a CNNM4-based therapy.

Preclinical Study of a siRNA CNNM4-Based Therapy

Figure 6:
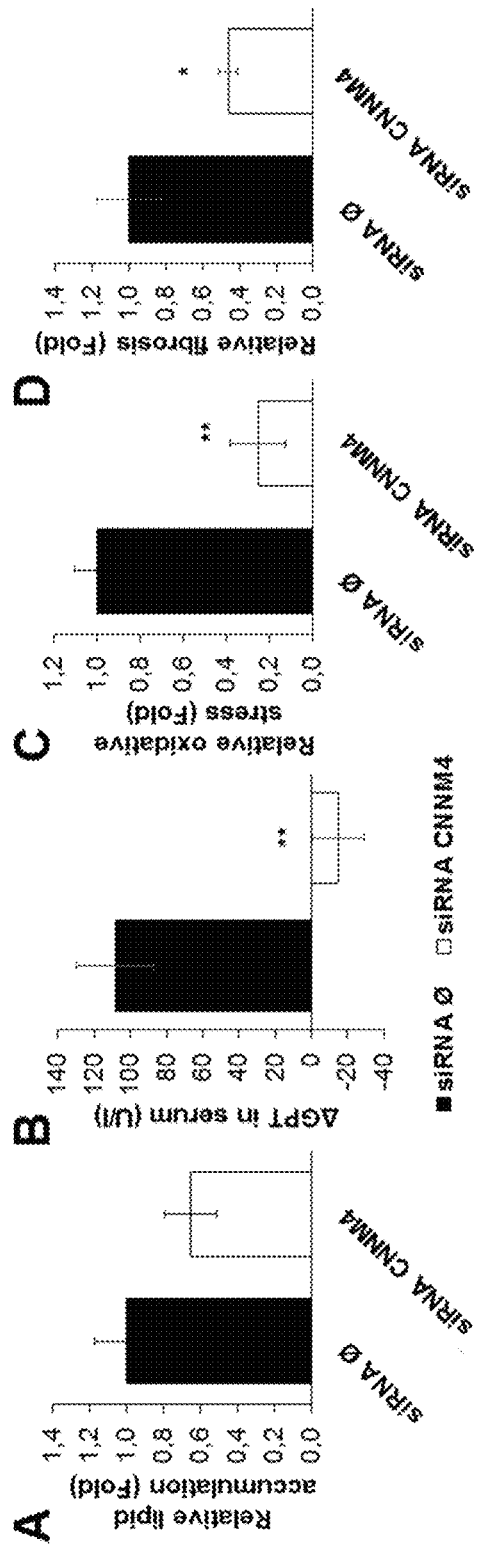
FIG. 6. Parameters analysed for observing NAFLD progression after siRNA CNNM4 therapy. A) Sudan Red as indicator of lipid content decrease, B) GPT in serum as indicator of liver damage, C) DHE as indicator of inflammation by ROS and D) αSMA as indicator of fibrosis. $*p<0.05$ vs siRNA Ø; $**p<0.01$ vs siRNA Ø.

For addressing the effectivity of CNNM4 modulation not only in cells but also in animals, a preclinical study in NAFLD, the first stage of chronic liver disease, was developed. Mice were fed a 0.1% methionine and choline-deficient diet (0.1% MCDD) during 2 weeks in order to develop NAFLD. At that time a group was treated with a siRNA CNNM4 therapy and another with a siCtrl RNA, following the 0.1% MCDD during 2 weeks. Animals were sacrificed and different biomarkers were measured in order to analyze NAFLD progression. Sudan red staining measured lipid accumulation (FIG. 6A), transaminases in serum indicate liver damage (FIG. 6B), DHE staining quantifies inflammation caused by ROS (FIG. 6C) and α-smooth-muscle actin (αSMA) shows the progression of fibrosis (FIG. 6D). It can be observed that in the group of animals treated with siRNA CNNM4 therapy NAFLD is reduced.

Pharmacological Inhibition of CNNM4

Figure 7:
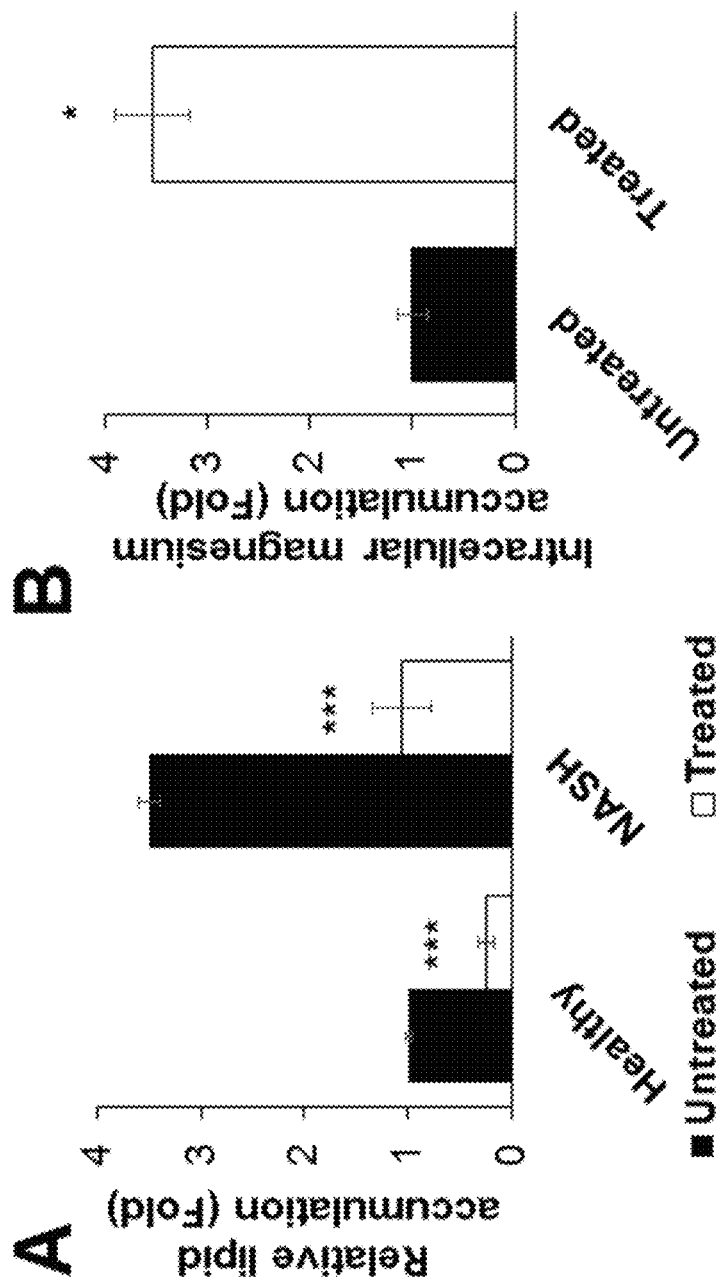
FIG. 7. Pharmacological inhibition of CNNM4 by the 7-amino-2-phenyl-5H-thieno[3,2-c]pyridin-4-one has the same effect in NASH-induced hepatocytes as siRNA CNNM4 therapy. A) Treated hepatocytes show reduced lipid levels and B) an increase of intracellular magnesium levels. $*p<0.05$ vs Untreated; $***p<0.001$ vs Untreated.

In addition to siRNA therapy, CNNM4 activity can be also modulated pharmacologically. An in vitro assay was performed inducing NASH in primary hepatocytes and treating them with a compound known as 7-amino-2-phenyl-5H-thieno[3,2-c]pyridin-4-one. It can be observed that this pharmacological inhibition of CNNM4 has the same effect as siRNA therapy in NASH-induced hepatocytes, it decreases its lipid content (FIG. 7A) and leads them to accumulate magnesium (FIG. 7B).

CNNM4 Over-Expression in Pathologies of Different Organs

Figure 8:
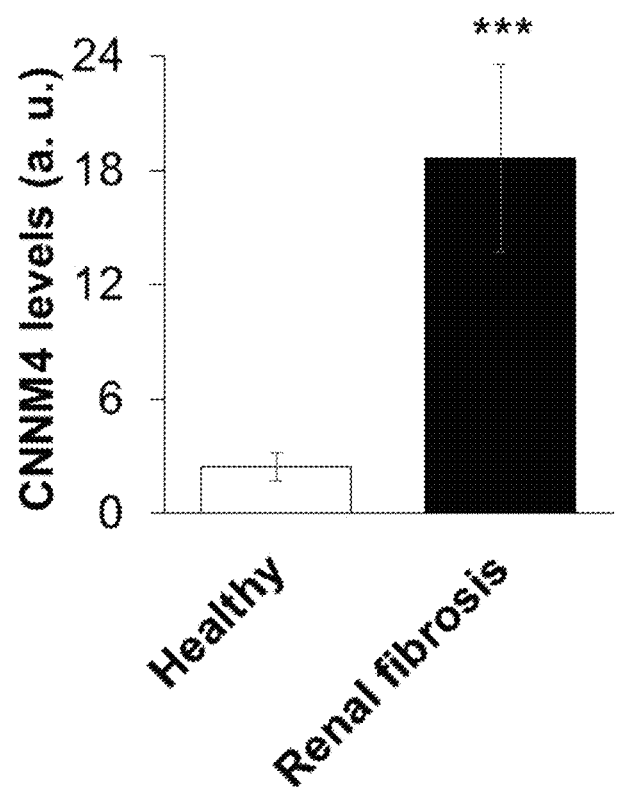
FIG. 8. CNNM4 expression determined by IHC in animal samples of renal fibrosis. $***p<0.001$ vs Healthy.
Figure 9:
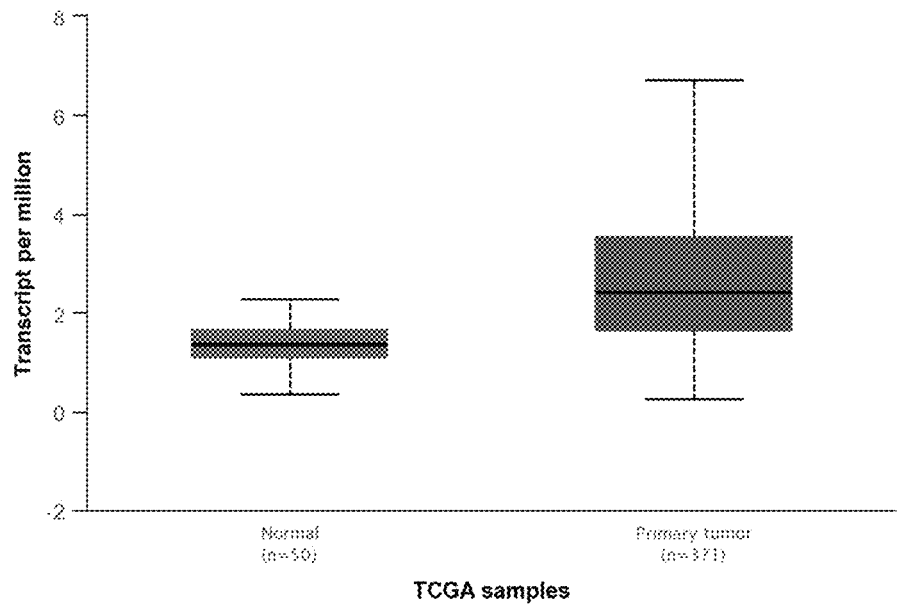
FIG. 9. A) CNNM4 expression determined in TCGA (The Cancer Genome Atlas) primary tumor samples of Liver Hepatocellular Carcinoma (LIHC) compared to normal tissue. B) CNNM4 expression determined in TCGA (The Cancer Genome Atlas) primary tumor samples of lung adenocarcinoma (LUAD) compared to normal tissue.
Figure 9:
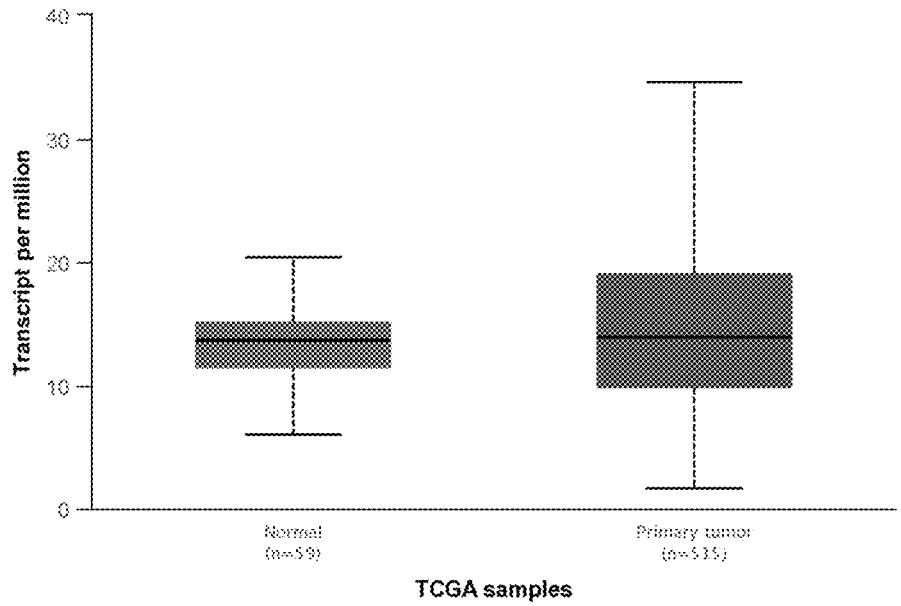

As shown in FIG. 1, CNNM4 has been found to be overexpressed in different liver pathologies both in animal model and in human samples. Particularly, fibrosis development occurs not only in liver but also in other organs such as kidney and, considering several similarities that the development of fibrosis may have in both tissues, CNNM4 may be also dysregulated this organ. It has been observed a CNNM4 overexpression in renal fibrosis mouse model, indicating a CNNM4-based therapy as an effective one for the treatment of the disease (FIG. 8). In addition, an analysis of TCGA (The Cancer Genome Atlas) data shows that CNNM4 is overexpressed in primary tumor samples of Liver Hepatocellular Carcinoma (LIHC) and in primary tumor samples of lung adenocarcinoma (LUAD) compared to normal tissue (FIGS. 9A and 9B).

In summary, the presented results prove that CNNM4 is a suitable target for preventing NAFLD progression and indicates that could also ameliorate the other liver pathologies (DILI, cirrhosis and HCC), renal fibrosis and lung cancer. In case of DILI, the in vitro studies show a protective effect of siRNA therapy from APAP overdose and, in the other pathologies, CNNM4 determination shows an overexpression in all of them. Therefore, inhibiting or silencing the protein or its partners, by siRNA therapy or pharmacologically, is a suitable method for treating liver disease, renal fibrosis and lung cancer.

The invention claimed is:

1. A method of treatment of an acute or a chronic disease in a subject, the method comprising administering a Cyclin and CBS domain divalent metal cation transport A mediator (CNNM4) inhibitor to said subject, wherein the CNNM4 inhibitor is selected from siRNA, RNA interference oligonucleotides, shRNA and dicer substrate 27-mer duplex, and wherein the disease is selected from:
- a liver disease selected from liver fibrosis, veno-occlusive liver disease, drug-induced liver injury (DILI), steatosis, non-alcoholic steatohepatitis (NASH), cirrhosis, hepatocellular carcinoma (HCC), primary biliary cirrhosis (PBC), primary sclerosing cholangitis, fatty liver, non-alcoholic fatty liver disease (NAFLD), alcoholic hepatitis, Budd-Chiari syndrome, or hepatitis;
- a kidney disease selected from acute kidney injury (AKI), chronic kidney disease, nephritis, nephrosis or renal fibrosis; or
- a lung disease selected from pulmonary fibrosis or lung adenocarcinoma.

2. The method according to claim 1,
wherein said liver disease is selected from drug-induced liver injury (DILI), non-alcoholic steatohepatitis (NASH), NAFLD or hepatocellular carcinoma (HCC);
wherein said kidney disease is renal fibrosis; or
wherein said lung disease is lung adenocarcinoma.

3. The method according to claim 1, wherein said CNNM4 inhibitor is siRNA.

* * * * *